US012232997B2

(12) United States Patent
Andersen et al.

(10) Patent No.: US 12,232,997 B2
(45) Date of Patent: Feb. 25, 2025

(54) ACCESSORY DEVICE OF A MEDICAL SYSTEM AND RELATED METHODS FOR ISSUE IDENTIFICATION

(71) Applicant: Coloplast A/S, Humlebaek (DK)

(72) Inventors: Dan Boegsted Andersen, Copenhagen OE (DK); Esben Stroebech, Hoersholm (DK); Marie Svane Rizk Vestergaard, Frederiksberg (DK)

(73) Assignee: Coloplast A/S, Humlebaek (DK)

( * ) Notice: Subject to any disclaimer, the term of this patent is extended or adjusted under 35 U.S.C. 154(b) by 866 days.

(21) Appl. No.: 17/268,481

(22) PCT Filed: Aug. 15, 2019

(86) PCT No.: PCT/DK2019/050243
§ 371 (c)(1),
(2) Date: Feb. 15, 2021

(87) PCT Pub. No.: WO2020/035121
PCT Pub. Date: Feb. 20, 2020

(65) Prior Publication Data
US 2021/0177642 A1 Jun. 17, 2021

(30) Foreign Application Priority Data
Aug. 15, 2018 (DK) .......................... PA 2018 70526

(51) Int. Cl.
A61F 5/44 (2006.01)
A61F 5/443 (2006.01)
(Continued)

(52) U.S. Cl.
CPC ............ A61F 5/4404 (2013.01); A61F 5/443 (2013.01); G16H 10/40 (2018.01); G16H 40/63 (2018.01); G16H 40/67 (2018.01)

(58) Field of Classification Search
CPC ........ A61F 5/4404; A61F 5/443; A61F 5/445; G16H 10/40; G16H 40/63; G16H 40/67; A61M 2205/3576
See application file for complete search history.

(56) References Cited

U.S. PATENT DOCUMENTS 2,054,535 A 9/1936 Diack
2,327,514 A 8/1943 Fenwick
(Continued)

FOREIGN PATENT DOCUMENTS

CA 2202199 C 8/2006
CN 203786580 U 8/2014
(Continued)

OTHER PUBLICATIONS

International Preliminary Report on Patentability received for PCT Patent Application No. PCT/DK2019/050243, mailed on Feb. 25, 2021, 12 pages.
(Continued)

Primary Examiner — Susan S Su
Assistant Examiner — Ted Yang
(74) Attorney, Agent, or Firm — Coloplast Corp., Coloplast A/S; Nick Baumann

(57) ABSTRACT

An accessory device includes an interface configured to communicate with one or more devices of an ostomy system and including a display. The ostomy system includes a monitor device and/or an ostomy appliance that is configured to be placed on a skin surface of a user. The ostomy appliance includes a base plate. A method performed in an accessory device includes obtaining monitor data from the monitor device that is indicative of presence of fluid at a proximal side of a first adhesive layer of the base plate towards the skin surface; determining an issue based on the monitor data that is related to the ostomy appliance; iden-
(Continued)

tifying, based on the determined issue, a set of candidate actions; selecting a set of digital content based on the set of candidate actions; and displaying the set of digital content on the display.

20 Claims, 16 Drawing Sheets

(51) Int. Cl.
*G16H 10/40* (2018.01)
*G16H 40/63* (2018.01)
*G16H 40/67* (2018.01)

(56) References Cited

U.S. PATENT DOCUMENTS

| | | |
|---|---|---|
| 2,542,233 A | 2/1951 | Carroll |
| 2,544,579 A | 3/1951 | Ardner |
| 3,214,502 A | 10/1965 | Schaar |
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,167,650 A | 12/1992 | Johnsen et al. |
| 5,197,895 A | 3/1993 | Stupecky |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,570,082 A | 10/1996 | Mahgerefteh et al. |
| 5,593,397 A | 1/1997 | La Gro |
| 5,626,135 A | 5/1997 | Sanfilippo |
| 5,672,163 A | 9/1997 | Ferreira et al. |
| 5,677,221 A | 10/1997 | Tseng |
| 5,704,905 A | 1/1998 | Jensen et al. |
| 5,790,036 A | 8/1998 | Fisher et al. |
| 5,800,415 A | 9/1998 | Olsen |
| 5,816,252 A | 10/1998 | Faries et al. |
| 5,834,009 A | 11/1998 | Sawers et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,057,689 A | 5/2000 | Saadat |
| 6,103,033 A | 8/2000 | Say et al. |
| 6,135,986 A | 10/2000 | Leisner et al. |
| 6,165,005 A | 12/2000 | Mills et al. |
| 6,171,289 B1 * | 1/2001 | Millot .................. A61F 5/443 604/336 |
| 6,206,864 B1 | 3/2001 | Kavanagh et al. |
| 6,246,330 B1 | 6/2001 | Nielsen |
| 6,297,422 B1 | 10/2001 | Hansen et al. |
| 6,407,308 B1 | 6/2002 | Roe et al. |
| 6,433,244 B1 | 8/2002 | Roe et al. |
| 6,482,491 B1 | 11/2002 | Samuelsen et al. |
| 6,485,476 B1 | 11/2002 | Von et al. |
| 6,520,943 B1 | 2/2003 | Wagner |
| 6,659,989 B1 | 12/2003 | Otto |
| 6,677,859 B1 | 1/2004 | Bensen |
| 6,764,474 B2 | 7/2004 | Nielsen et al. |
| 7,049,478 B1 | 5/2006 | Smith |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,221,279 B2 | 5/2007 | Nielsen |
| 7,326,190 B2 | 2/2008 | Botten |
| 7,341,578 B2 | 3/2008 | Bulow et al. |
| 7,347,844 B2 | 3/2008 | Cline et al. |
| 7,367,965 B2 | 5/2008 | Poulsen et al. |
| 7,422,578 B2 | 9/2008 | Shan et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 * | 3/2010 | McCall .................. A61M 1/3655 210/651 |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,398,575 B1 * | 3/2013 | McCall .................. A61M 1/3656 604/4.01 |
| 8,398,603 B2 * | 3/2013 | Thirstrup .................. A61B 5/746 602/41 |
| 8,399,732 B2 | 3/2013 | Oelund et al. |
| 8,409,158 B2 | 4/2013 | Edvardsen et al. |
| 8,449,471 B2 | 5/2013 | Tran |
| 8,474,338 B2 | 7/2013 | Gelman et al. |
| 8,500,718 B2 | 8/2013 | Locke et al. |
| 8,632,492 B2 | 1/2014 | Delegge |
| 8,680,991 B2 | 3/2014 | Tran |
| 8,684,982 B2 | 4/2014 | Nguyen-Demary et al. |
| 8,740,865 B2 | 6/2014 | Krystek et al. |
| 8,795,257 B2 | 8/2014 | Coulthard et al. |
| D712,545 S | 9/2014 | Igwebuike et al. |
| 8,821,464 B2 | 9/2014 | Hanuka et al. |
| 8,975,465 B2 | 3/2015 | Hong et al. |
| 8,979,813 B2 | 3/2015 | Uveborn |
| 9,046,085 B2 | 6/2015 | Schoess et al. |
| 9,066,812 B2 | 6/2015 | Edvardsen et al. |
| 9,216,104 B2 * | 12/2015 | Thirstrup .................. A61F 5/4404 |
| 9,308,332 B2 | 4/2016 | Heppe |
| 9,322,797 B1 | 4/2016 | Lastinger et al. |
| 9,629,779 B2 | 4/2017 | Grum-Schwensen et al. |
| 9,629,964 B2 | 4/2017 | Wuepper |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 * | 7/2018 | Thirstrup .................. A61F 13/42 |
| D826,740 S | 8/2018 | Stevens et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 * | 4/2021 | Thirstrup .................. A61B 5/746 |
| 11,096,818 B2 * | 8/2021 | Thirstrup .................. A61F 13/02 |
| 11,135,084 B2 | 10/2021 | Seres et al. |
| 11,306,224 B2 | 4/2022 | Chatterjee et al. |
| 11,406,525 B2 | 8/2022 | Seres et al. |
| 11,471,318 B2 | 10/2022 | Hansen et al. |
| 11,491,042 B2 | 11/2022 | Seres et al. |
| 11,534,323 B2 | 12/2022 | Hansen et al. |
| 11,540,937 B2 | 1/2023 | Hansen et al. |
| 11,547,595 B2 | 1/2023 | Hansen et al. |
| 11,547,596 B2 | 1/2023 | Hansen et al. |
| 11,559,423 B2 | 1/2023 | Speiermann et al. |
| 11,559,426 B2 | 1/2023 | Sletten et al. |
| 2002/0019615 A1 | 2/2002 | Roe et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |

(56) References Cited

U.S. PATENT DOCUMENTS

| | | |
|---|---|---|
| 2004/0049145 A1 | 3/2004 | Flick |
| 2004/0068244 A1 | 4/2004 | Salone et al. |
| 2004/0078219 A1 | 4/2004 | Kaylor et al. |
| 2004/0100376 A1 | 5/2004 | Lye et al. |
| 2004/0106908 A1 | 6/2004 | Leise et al. |
| 2004/0111072 A1 | 6/2004 | McKissick |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries et al. |
| 2006/0271002 A1 | 11/2006 | Botten |
| 2007/0010256 A1 | 1/2007 | Klabunde et al. |
| 2007/0035405 A1 | 2/2007 | Wada et al. |
| 2007/0135782 A1 | 6/2007 | Bager et al. |
| 2007/0142796 A1 | 6/2007 | Mosbacher et al. |
| 2007/0185464 A1 | 8/2007 | Fattman et al. |
| 2007/0204691 A1* | 9/2007 | Bogner ............... A61B 5/6892 73/432.1 |
| 2008/0038536 A1 | 2/2008 | Strobech et al. |
| 2008/0041792 A1* | 2/2008 | Crnkovich ............ A61M 1/367 210/739 |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0096726 A1 | 4/2008 | Riley et al. |
| 2008/0097360 A1 | 4/2008 | Andersen et al. |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0300578 A1* | 12/2008 | Freedman ............ A61M 1/966 600/587 |
| 2008/0306459 A1 | 12/2008 | Albrectsen |
| 2009/0009342 A1 | 1/2009 | Karjalainen |
| 2009/0012501 A1 | 1/2009 | Boehringer et al. |
| 2009/0118600 A1 | 5/2009 | Ortiz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0216169 A1 | 8/2009 | Hansen et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1* | 2/2010 | Thirstrup ............ A61F 5/4404 340/657 |
| 2010/0036206 A1 | 2/2010 | Lorio |
| 2010/0072271 A1 | 3/2010 | Thorstensson |
| 2010/0076275 A1 | 3/2010 | Chu et al. |
| 2010/0114047 A1* | 5/2010 | Song ..................... A61F 13/42 604/361 |
| 2010/0271212 A1* | 10/2010 | Page ..................... A61F 13/42 340/573.1 |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2011/0245682 A1* | 10/2011 | Robinson ............. G01M 3/002 600/473 |
| 2012/0013130 A1 | 1/2012 | Jung |
| 2012/0143154 A1* | 6/2012 | Edvardsen ........... A61F 5/4404 604/336 |
| 2012/0143155 A1 | 6/2012 | Edvardsen et al. |
| 2012/0172673 A1 | 7/2012 | Friedman et al. |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1 | 11/2012 | Nguyen-Demary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165821 A1* | 6/2013 | Freedman ............ A61M 3/0279 604/20 |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1* | 9/2013 | Thirstrup ............. A61F 5/445 604/344 |
| 2013/0254141 A1 | 9/2013 | Barda et al. |
| 2013/0261575 A1 | 10/2013 | Kiyoshi |
| 2013/0267790 A1 | 10/2013 | Pfuetzner et al. |
| 2013/0303867 A1 | 11/2013 | Elfstrom et al. |
| 2013/0307570 A1 | 11/2013 | Bosaeus et al. |
| 2013/0324952 A1* | 12/2013 | Krystek ................ A61F 5/445 604/318 |
| 2013/0324955 A1 | 12/2013 | Wong et al. |
| 2014/0051946 A1 | 2/2014 | Arne et al. |
| 2014/0133290 A1 | 5/2014 | Yokoo et al. |
| 2014/0200538 A1* | 7/2014 | Euliano ................ A61F 13/42 604/361 |
| 2014/0236111 A1 | 8/2014 | Casado et al. |
| 2014/0236335 A1 | 8/2014 | Lewis et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0303574 A1 | 10/2014 | Knutson |
| 2014/0309600 A1* | 10/2014 | Aceto ..................... A61M 1/73 604/319 |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0231802 A1 | 8/2015 | Quan et al. |
| 2015/0250639 A1* | 9/2015 | Thirstrup ........... A61F 13/00051 156/278 |
| 2015/0257923 A1* | 9/2015 | Thirstrup ............. A61F 13/42 604/318 |
| 2015/0342777 A1* | 12/2015 | Seres ..................... A61F 5/44 604/318 |
| 2015/0351690 A1 | 12/2015 | Toth et al. |
| 2015/0374896 A1 | 12/2015 | Du et al. |
| 2016/0015570 A1 | 1/2016 | Heinecke et al. |
| 2016/0084869 A1 | 3/2016 | Yuen et al. |
| 2016/0158056 A1 | 6/2016 | Davis et al. |
| 2016/0158517 A1* | 6/2016 | Nebbia ................. A61M 5/158 604/111 |
| 2016/0158969 A1 | 6/2016 | McLane et al. |
| 2016/0166438 A1 | 6/2016 | Rovaniemi |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0284084 A1 | 9/2016 | Gurcan et al. |
| 2016/0305776 A1 | 10/2016 | Mrtensson et al. |
| 2016/0310140 A1 | 10/2016 | Belson et al. |
| 2016/0310329 A1 | 10/2016 | Patel et al. |
| 2016/0317728 A1 | 11/2016 | Lewis et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079530 A1 | 3/2017 | DiMaio et al. |
| 2017/0079576 A1 | 3/2017 | Stroebech et al. |
| 2017/0098044 A1 | 4/2017 | Lai et al. |
| 2017/0112658 A1 | 4/2017 | Hosono |
| 2017/0140103 A1* | 5/2017 | Angelides ........... A61F 5/4404 |
| 2017/0156920 A1 | 6/2017 | Hunt et al. |

(56) References Cited

U.S. PATENT DOCUMENTS

| | | |
|---|---|---|
| 2017/0262986 A1 | 9/2017 | Xiong et al. |
| 2017/0319073 A1 | 11/2017 | DiMaio et al. |
| 2017/0340474 A1* | 11/2017 | Thirstrup ............... A61B 5/746 |
| 2017/0348137 A1 | 12/2017 | Hvid et al. |
| 2017/0348162 A1 | 12/2017 | Arizti et al. |
| 2017/0360592 A1 | 12/2017 | Carrubba |
| 2017/0367654 A1 | 12/2017 | Cheng et al. |
| 2018/0021164 A1 | 1/2018 | Fenton |
| 2018/0021165 A1 | 1/2018 | Fenton |
| 2018/0049667 A1 | 2/2018 | Heppe |
| 2018/0055359 A1 | 3/2018 | Shamim et al. |
| 2018/0078163 A1 | 3/2018 | Welch |
| 2018/0109852 A1 | 4/2018 | Mandapaka et al. |
| 2018/0171183 A1 | 6/2018 | Sakurai et al. |
| 2018/0177626 A1 | 6/2018 | Israelson |
| 2018/0250156 A1 | 9/2018 | Lam |
| 2018/0298240 A1 | 10/2018 | Chatterjee et al. |
| 2018/0318475 A1* | 11/2018 | Thomson ................. A61M 1/90 |
| 2018/0344533 A1 | 12/2018 | Rovaniemi |
| 2019/0008439 A1 | 1/2019 | Sageder et al. |
| 2019/0099552 A1 | 4/2019 | Zhang et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1* | 5/2019 | Schoess ............... A61F 5/4404 604/336 |
| 2019/0175386 A1 | 6/2019 | Monty |
| 2019/0192066 A1 | 6/2019 | Schoess et al. |
| 2019/0192332 A1* | 6/2019 | Hansen ............. A61F 13/00055 |
| 2019/0192333 A1 | 6/2019 | Hansen et al. |
| 2019/0192334 A1 | 6/2019 | Hansen et al. |
| 2019/0240059 A1* | 8/2019 | Seres ..................... A61F 5/445 |
| 2019/0247050 A1 | 8/2019 | Goldsmith |
| 2019/0374163 A1 | 12/2019 | Faarbaek et al. |
| 2019/0374372 A1 | 12/2019 | Seres et al. |
| 2020/0100931 A1 | 4/2020 | Schoess et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Munoz Herencia |
| 2020/0297244 A1 | 9/2020 | Brownhill et al. |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0375809 A1* | 12/2020 | Sullivan ................. A61F 13/42 |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0386368 A1 | 12/2021 | Carlsson et al. |
| 2022/0000652 A1* | 1/2022 | Thirstrup ................ A61F 5/443 |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |
| 2022/0378602 A1 | 12/2022 | Hansen et al. |
| 2023/0059470 A1 | 2/2023 | Hansen et al. |
| 2023/0064734 A1 | 3/2023 | Hansen et al. |
| 2023/0105402 A1 | 4/2023 | Hansen et al. |
| 2023/0117727 A1 | 4/2023 | Hansen et al. |
| 2023/0118594 A1 | 4/2023 | Speiermann et al. |
| 2023/0145670 A1 | 5/2023 | Seres et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |

FOREIGN PATENT DOCUMENTS

| | | |
|---|---|---|
| CN | 104902399 A | 9/2015 |
| CN | 104980878 A | 10/2015 |
| CN | 105588856 A | 5/2016 |
| CN | 206271160 U | 6/2017 |
| CN | 206450708 U | 8/2017 |
| CN | 107661167 A | 2/2018 |
| DE | 3437950 A1 | 4/1985 |
| DE | 3836590 A1 | 5/1990 |
| DE | 19900611 C1 | 7/2000 |
| DE | 69722993 T2 | 7/2004 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0800804 A1 | 10/1997 |
| EP | 1275357 A2 | 1/2003 |
| EP | 1188157 B1 | 12/2005 |
| EP | 2000083 A2 | 12/2008 |
| EP | 2108345 A1 | 10/2009 |
| EP | 2453851 A2 | 5/2012 |
| EP | 2489561 A2 | 8/2012 |
| EP | 2601915 A1 | 6/2013 |
| EP | 2654646 A2 | 10/2013 |
| EP | 2738960 A1 | 6/2014 |
| EP | 3064179 A1 | 9/2016 |
| EP | 3213727 A1 | 9/2017 |
| EP | 3226946 A1 | 10/2017 |
| GB | 2219679 A | 12/1989 |
| GB | 2225951 A | 6/1990 |
| GB | 2308306 A | 6/1997 |

(56) References Cited

FOREIGN PATENT DOCUMENTS

| | | | |
|---|---|---|---|
| GB | 2343628 A | 5/2000 | |
| GB | 2465742 A | 6/2010 | |
| GB | 2486968 A | 7/2012 | |
| GB | 2542093 A | 3/2017 | |
| GB | 2561193 A | 10/2018 | |
| JP | 04-074882 A | 3/1992 | |
| JP | 06-152077 A | 5/1994 | |
| JP | 09-010184 A | 1/1997 | |
| JP | 2000-093448 A | 4/2000 | |
| JP | 2001-087299 A | 4/2001 | |
| JP | 2002-055074 A | 2/2002 | |
| JP | 2002-224093 A | 8/2002 | |
| JP | 2005-323981 A | 11/2005 | |
| JP | 2007-319561 A | 12/2007 | |
| JP | 2009-519751 A | 5/2009 | |
| JP | 2014-033745 A | 2/2014 | |
| JP | 2014-054368 A | 3/2014 | |
| KR | 10-1056989 B1 | 8/2011 | |
| KR | 10-2012-0003987 A | 1/2012 | |
| KR | 20-0485138 Y1 | 12/2017 | |
| NL | 1001019 C2 | 2/1997 | |
| NL | 1003904 C2 | 3/1998 | |
| RU | 2527155 C2 | 8/2014 | |
| TW | 201201783 A | 1/2012 | |
| WO | 94/15562 A1 | 7/1994 | |
| WO | 97/10012 A1 | 3/1997 | |
| WO | 99/33037 A1 | 7/1999 | |
| WO | 99/36017 A1 | 7/1999 | |
| WO | 00/79497 A1 | 12/2000 | |
| WO | 01/13830 A1 | 3/2001 | |
| WO | 01/50996 A1 | 7/2001 | |
| WO | 02/52302 A2 | 7/2002 | |
| WO | 02/99765 A1 | 12/2002 | |
| WO | 2005/038693 A1 | 4/2005 | |
| WO | 2005/082271 A2 | 9/2005 | |
| WO | 2006/008866 A1 | 1/2006 | |
| WO | 2006/094513 A2 | 9/2006 | |
| WO | 2007/000168 A1 | 1/2007 | |
| WO | 2007/059774 A2 | 5/2007 | |
| WO | 2007/070266 A1 | 6/2007 | |
| WO | WO-2007098762 A1 * | 9/2007 | ............. A61B 5/746 |
| WO | 2007/133555 A2 | 11/2007 | |
| WO | 2007128038 A1 | 11/2007 | |
| WO | 2008/057884 A2 | 5/2008 | |
| WO | 2009/006900 A1 | 1/2009 | |
| WO | 2009/052496 A1 | 4/2009 | |
| WO | 2009/107011 A1 | 9/2009 | |
| WO | 2009/112912 A2 | 9/2009 | |
| WO | 2011/003421 A1 | 1/2011 | |
| WO | 2011/004165 A1 | 1/2011 | |
| WO | 2011/007355 A2 | 1/2011 | |
| WO | 2011/061540 A1 | 5/2011 | |
| WO | 2011/105701 A2 | 9/2011 | |
| WO | 2011/123018 A1 | 10/2011 | |
| WO | 2011/139499 A1 | 11/2011 | |
| WO | 2011/161254 A2 | 12/2011 | |
| WO | 2012068386 A1 | 5/2012 | |
| WO | 2012/076022 A2 | 6/2012 | |
| WO | 2012/084987 A2 | 6/2012 | |
| WO | 2013/013197 A1 | 1/2013 | |
| WO | 2013095231 A1 | 6/2013 | |
| WO | 2014/004207 A1 | 1/2014 | |
| WO | 2014/086369 A1 | 6/2014 | |
| WO | 2015/007284 A1 | 1/2015 | |
| WO | 2015/014774 A1 | 2/2015 | |
| WO | 2015/084462 A1 | 6/2015 | |
| WO | 2015/094064 A1 | 6/2015 | |
| WO | 2015/187366 A1 | 12/2015 | |
| WO | WO-2015186452 A1 * | 12/2015 | ............. A61F 5/445 |
| WO | 2016/132738 A1 | 8/2016 | |
| WO | 2016/166731 A1 | 10/2016 | |
| WO | 2016162038 A1 | 10/2016 | |
| WO | 2016/192738 A1 | 12/2016 | |
| WO | 2017/023794 A1 | 2/2017 | |
| WO | 2017/062042 A1 | 4/2017 | |
| WO | 2017/067558 A1 | 4/2017 | |
| WO | 2017/067560 A1 | 4/2017 | |
| WO | 2017/074505 A1 | 5/2017 | |
| WO | 2017/088153 A1 | 6/2017 | |
| WO | 2017108109 A1 | 6/2017 | |
| WO | 2017/136696 A1 | 8/2017 | |
| WO | 2017/190752 A1 | 11/2017 | |
| WO | 2018/028756 A1 | 2/2018 | |
| WO | WO-2019094635 A1 * | 5/2019 | ............. A61B 5/002 |
| WO | 2019/120432 A1 | 6/2019 | |
| WO | 2019/161859 A1 | 8/2019 | |
| WO | 2019/161860 A1 | 8/2019 | |
| WO | 2019161863 A1 | 8/2019 | |
| WO | 2019/174693 A1 | 9/2019 | |
| WO | 2019/174695 A1 | 9/2019 | |
| WO | 2019/213623 A1 | 11/2019 | |
| WO | 2020/035121 A1 | 2/2020 | |

OTHER PUBLICATIONS

International Search Report and Written Opinion received for PCT Patent Application No. PCT/DK2019/050243, mailed on Nov. 25, 2019, 15 pages.

\* cited by examiner

ACCESSORY DEVICE OF A MEDICAL SYSTEM AND RELATED METHODS FOR ISSUE IDENTIFICATION

The present disclosure relates to an accessory device of an ostomy system and related methods, e.g. for monitoring an ostomy appliance and/or assisting a user of the ostomy system. The ostomy system comprises an ostomy appliance, an accessory device, and a monitor device. In particular, the present disclosure relates to methods and devices for improved assisting and guiding of a user.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
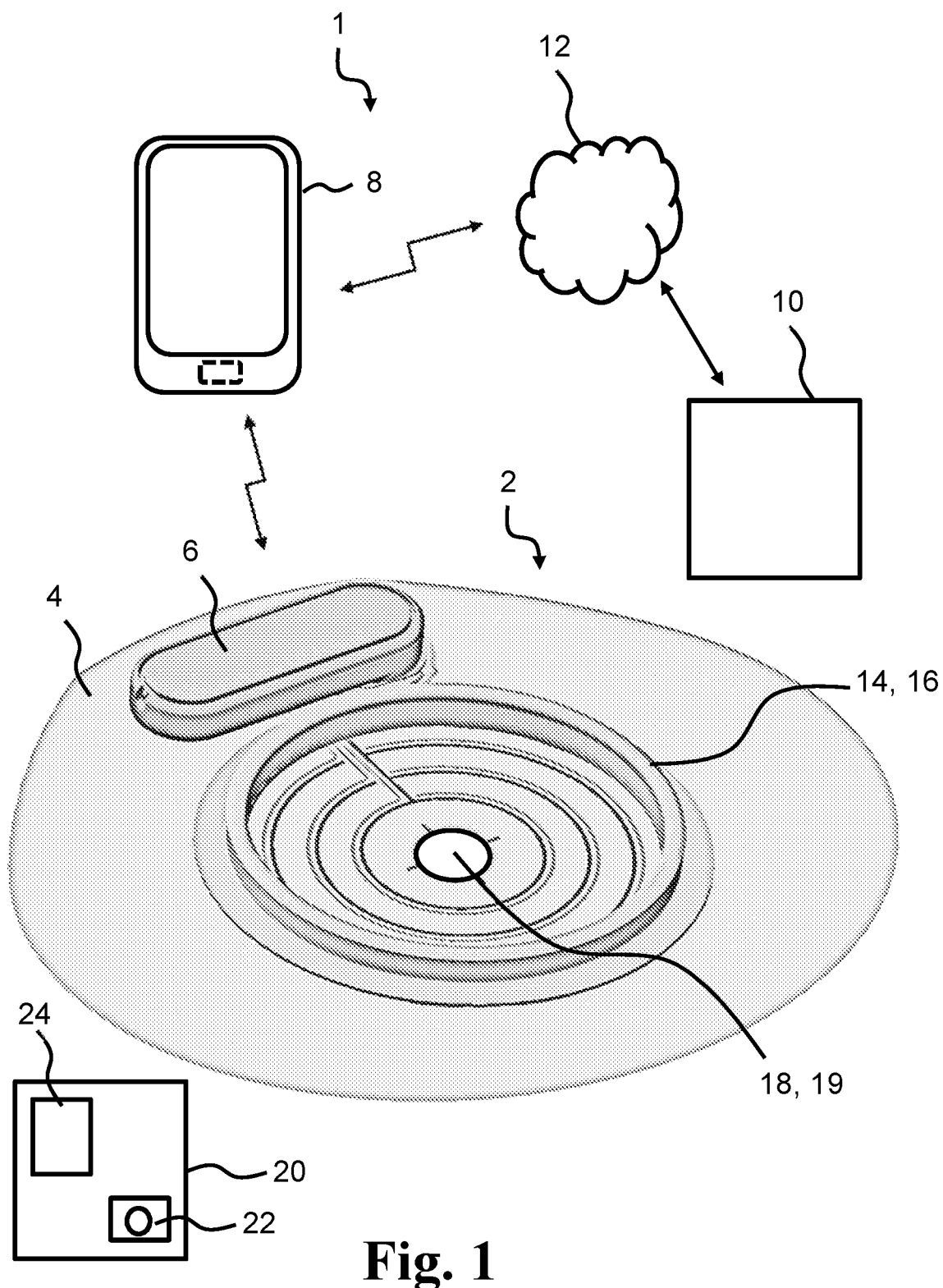
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to an accessory device of the ostomy system and accessory devices thereof are disclosed. An accessory device (also referred to as an external device) may be a mobile phone or other handheld device. An accessory device may be a personal electronic device, e.g. a wearable, such as a watch or other wrist-worn electronic device. The ostomy system may comprise a docking station. An accessory device may be a docking station. An accessory device may act as a docking station. The docking station may be configured to electrically and/or mechanically couple the monitor device to the docking station. The docking station may be configured for charging the monitor device and/or configured for transferring data between the monitor device and the docking station, and/or between the accessory device and the docking station and/or between the monitor device and the accessory device via the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive material, the ostomy system and devices thereof enable providing information to the user about the type of failure, and in turn enable providing customized indications to the user of appropriate actions to be made for improving the use of the ostomy appliance without experiencing severe leakage and/or skin damage.

The present disclosure provides a method, optionally performed in an accessory device, wherein the accessory device comprises an interface configured to communicate with one or more devices of an ostomy system, the interface comprising a display, wherein the ostomy system comprises a monitor device and/or an ostomy appliance, the ostomy appliance being configured to be placed on a skin surface of a user, wherein the ostomy appliance comprises a base plate, the method comprising: obtaining monitor data from the monitor device, wherein the monitor data is optionally indicative of presence of fluid, such as urine, output, sweat and/or mucus, at a proximal side of a first adhesive layer of the base plate towards the skin surface and/or indicative of a moisture level in a first adhesive layer of the base plate; determining an issue based on the monitor data, wherein the issue is related to the ostomy appliance; identifying, based on the determined issue, a set of candidate actions to the issue from a plurality of possible actions; selecting a set of digital content based on the set of candidate actions; and displaying the set of digital content on the display.

Also disclosed is an accessory device, wherein the accessory device forms part of an ostomy system, the accessory device comprising a memory; a processor operatively connected to the memory; and an interface operatively connected to the processor and configured to communicate with one or more devices of the ostomy system, the one or more devices comprising a monitor device and/or an ostomy appliance configured to be placed on a skin surface of a user, the ostomy appliance comprising a base plate, wherein the interface is configured to obtain monitor data from the one or more devices, and wherein the interface comprises a display, wherein the processor is configured to determine an issue based on the monitor data, wherein the issue is related to the ostomy appliance; identify a set of candidate actions from a plurality of possible actions based on the determined issue; select a set of digital content based on the set of candidate actions; and wherein the interface is configured to display the set of digital content on the display.

It is an advantage of the present disclosure that an optimum or improved use of an ostomy appliance is provided for. In particular, the present disclosure facilitates that a user is able to improve handling of the ostomy appliance before or during use in turn providing an improved (extended) wear time of the base plate/ostomy appliance and/or a reduced risk of skin damage to the user.

The present disclosure provides an efficient, and easy-to-use ostomy system with a high degree of comfort for a user.

Further, the present disclosure is useful in aiding to reduce the risk of a user experiencing leakage from an ostomy appliance and/or improving use (less skin irritation and/or increased wear time) of an ostomy appliance by providing a customized training tool with guidance to an improved preparation and/or use of the ostomy appliance. Further, the present disclosure is further useful in helping reduce the risk of skin damage to a user by providing customized and personalized guidance based on monitor data originating from the user.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area. The base plate may be planar or curved, such as concave or convex.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

A base plate and/or a sensor assembly part for an ostomy appliance is disclosed, the base plate and/or the sensor assembly part comprising a first adhesive layer with a proximal side configured for attachment of the base plate and/or the sensor assembly part to the skin surface of a user, the first adhesive layer having a stomal opening with a centre point; and a plurality of electrodes including a first leakage electrode, a second leakage electrode, and optionally a third leakage electrode, wherein the plurality of electrodes is configured to detect presence of fluid on the proximal side of the first adhesive layer in a primary sensing zone and/or a secondary sensing zone. The primary sensing zone is arranged in a primary angle space from the centre point of the first adhesive layer and the secondary sensing zone is arranged in a secondary angle space from the centre point of the first adhesive layer.

Further, a monitor device for an ostomy system is disclosed, the ostomy system comprising an ostomy appliance with a base plate having a first adhesive layer with a proximal side configured for attachment of the base plate and/or the sensor assembly part to the skin surface of a user, the first adhesive layer having a stomal opening with a centre point, the monitor device comprising a processor; memory; a first interface connected to the processor and the memory, the first interface configured for obtaining ostomy data from the base plate and/or the sensor assembly part coupled to the first interface; and a second interface connected to the processor and configured for transmitting monitor data to one or more accessory devices. The monitor data may be indicative of presence of fluid in the primary sensing zone, e.g. on the proximal side of the base plate and/or the sensor assembly part. The monitor data may be indicative of presence of fluid in the secondary sensing zone, e.g. on the proximal side of the base plate and/or the sensor assembly part. The monitor data may be indicative of presence of fluid in a tertiary sensing zone, e.g. on the proximal side of the base plate and/or the sensor assembly part. The memory of the monitor device may be configured for storing ostomy data. In one or more exemplary methods, the monitor data comprises ostomy data and/or parameter data. For example, the parameter data is derived based on ostomy data. Ostomy data and/or parameter data based on the ostomy data are obtained from electrodes/sensors of the ostomy appliance with e.g. a monitor device or an accessory device. The monitor device may be configured to process the ostomy data and/or parameter data based on the ostomy data to determine monitor data that are transmitted to the accessory device. The monitor data may be indicative of or comprise a moisture pattern type. The monitor data may be indicative of or comprise a wear time of the baseplate. The monitor device may be electrically coupled to the plurality of electrodes of the base plate and/or the sensor assembly part. For example, the monitor device may be couplable, such as releasably couplable, to the plurality of electrodes of the base plate and/or the sensor assembly part. The monitor device may be configured to measure one or more resistances between the plurality of electrodes and detect the leakage of output based on the measured one or more resistances.

Also disclosed is an ostomy system comprising an ostomy appliance and a monitor device as described herein.

The method comprises obtaining monitor data from the monitor device. The monitor data may be indicative of presence of fluid at a proximal side of a first adhesive layer of the base plate and/or the sensor assembly part towards the skin surface and/or indicative of a moisture level or moisture pattern in a first adhesive layer of the base plate and/or the sensor assembly part. In other words, the monitor data may be indicative of presence of fluid between the base plate and/or the sensor assembly part and the skin surface of the user. The monitor data may comprise ostomy data and/or parameter data. In one or more exemplary methods, obtaining monitor data comprises obtaining data representative of the measurements of the electrical properties at the proximal side of, within and/or at the distal side of the first adhesive layer. In one or more exemplary methods, the ostomy data and/or parameter data are indicative of resistance between any two of a plurality of electrodes, capacitance and/or inductance between any two of a plurality of electrodes and/or any change thereof. In one or more exemplary methods, the ostomy data and/or parameter data are indicative of a change in resistance, capacitance and/or inductance between electrodes. In one or more exemplary methods, the ostomy data and/or parameter data comprises timing information, such as timestamped data or information from which timing is derivable.

The method comprises determining an issue based on the monitor data, wherein the issue is related to the ostomy appliance. Determining an issue based on the monitor data may comprise determining one or more, such as a plurality of issues, based on the monitor data. An exemplary issue may be irregularities in the skin surface. An exemplary issue may be inappropriate application, such as insufficient pressure at application and/or inappropriate positioning, of the ostomy appliance. An exemplary issue may be use of a sub-optimal or inappropriate ostomy appliance type (concave, convex, one-part, two-part). An exemplary issue may be inappropriate preparation, such as cleaning and/or drying, of the skin surface. An exemplary issue may be inappropriate preparation of the base plate and/or the sensor assembly part, e.g. resulting from inappropriate or wrong cutting of base plate and/or the sensor assembly part. An exemplary issue may be a deviation from the standard/appropriate use, such as wear time, of the ostomy appliance. An exemplary issue may be change in intake, such as diet and/or medicine. An exemplary issue may be change in medicine. An exemplary issue may be change in physical activity. In the present context an issue may result (or is likely to result) in premature leakage between the base plate and/or the sensor assembly part and the skin of the user.

Determining an issue may comprise selecting an issue from a set of candidate issues based on the monitor data. Determining an issue may comprise to obtain an issue, e.g. from a server device. Accordingly, the method may comprise transmitting the monitor data (or parts thereof) to a server device and receiving an issue (or one or more issue parameters) from the server device.

In one or more exemplary methods, determining the issue based on the monitor data comprises determining one or more moisture pattern types, e.g. from a set of candidate moisture pattern types, based on the monitor data. A moisture pattern type is indicative of the distribution of fluid on the proximal side of the base plate and/or the sensor assembly part/first adhesive layer. A moisture pattern type may be indicative of the distribution of fluid in the first adhesive layer. An exemplary issue may be change in moisture pattern type compared to previous moisture pattern types. The set of candidate moisture pattern types may comprise a plurality of moisture pattern types, such as at least three different moisture pattern types. Determining an issue may comprise obtaining, e.g. determining and/or retrieving, a default moisture pattern type, comparing the current moisture pattern type with the default moisture pattern type, and optionally setting the issue to change in moisture pattern types if the difference between the current moisture pattern type and the default moisture pattern type satisfies a pattern change criterion. The default moisture pattern type may be based on monitor data for previous base plate and/or sensor assembly part wear cycles of the user. An exemplary issue may be change in wear time of the base plate and/or the sensor assembly part compared to previous wear times for previous base plate and/or sensor assembly part wear cycles. Determining an issue may comprise obtaining, e.g. determining and/or retrieving, a default wear time of base plates and/or sensor assembly parts, comparing the current wear time of the base plate and/or the sensor assembly part with the default wear time, and optionally setting the issue to change in wear time if the difference between the current wear time and the default wear time satisfies a wear time change criterion, e.g. if the difference between current wear time and the default wear time is larger than a wear time change threshold. Determining the issue based on the monitor data may be based on the moisture pattern type and the wear time of the base plate and/or the sensor assembly part. The method may comprise displaying an issue user interface element on the display, wherein the issue user interface element corresponds to or is indicative of the issue.

In the method, determining an issue based on the monitor data may comprise determining one or more wear time parameters, e.g. wear time, average wear time, and/or expected wear time, based on the monitor data, and wherein the issue is based on wear time parameter(s) of the one or more wear time parameters.

In the method, determining an issue may comprise selecting an issue from a look-up-table in a memory of the accessory device. The look-up table may map one or more moisture pattern types and/or one or more wear time parameters (e.g. wear time, average wear time, expected wear time) to an issue.

An exemplary moisture pattern type is a (first) directional moisture pattern type (directional leakage), i.e. a leakage primarily occurs or only occurs (is detected) in one (primary) sensing zone (in primary moisture pattern direction) out of a plurality of sensing zones. An exemplary moisture pattern type is a (second) directional moisture pattern type (directional leakage), i.e. a leakage primarily occurs or only occurs (is detected) in one (secondary) sensing zone (in secondary moisture pattern direction) out of a plurality of sensing zones. An exemplary moisture pattern type is a (third) directional moisture pattern type (directional leakage), i.e. a leakage primarily occurs or only occurs (is detected) in one (tertiary) sensing zone (in tertiary moisture pattern direction) out of a plurality of sensing zones. An exemplary moisture pattern type is a (fourth) directional moisture pattern type (directional leakage), i.e. a leakage primarily occurs or only occurs (is detected) in a subset of, e.g. two, sensing zones out of a plurality of sensing zones. An exemplary moisture pattern type is an omni-directional moisture pattern (omni-directional leakage), i.e. a leakage is distributed circumferentially around the stomal opening, i.e. a leakage occurs in all sensing zones of the base plate and/or the sensor assembly part. In one or more exemplary methods, determining one or more moisture pattern types based on the monitor data comprises identifying a moisture pattern type based on parameter data (of the monitor data). A moisture pattern type may comprise a moisture pattern direction, e.g. a main direction extending from the stomal opening.

Determining the issue based on the monitor data may comprise determining a leakage state of the ostomy appliance based on the monitor data.

In one or more exemplary methods, determining the issue based on the monitor data comprises generating a set of representative features of the moisture pattern type based on previously determined moisture pattern types (for previous base plates and/or sensor assembly parts); determining whether one or more features of the determined moisture pattern type satisfy a first issue criterion, wherein the first issue criterion is based on the set of representative features; and determining the issue as a first issue in accordance with the one or more features of the determined moisture pattern type satisfying the first issue criterion.

In one or more exemplary methods, determining the issue based on the monitor data comprises determining a number of occurrences of the determined moisture pattern type over a time period, such as at least 10 days or at least 10 base plate and/or sensor assembly part wear cycles; determining whether the number of occurrences satisfies a second issue criterion; and determining the issue as a second issue in accordance with the number of occurrences satisfying the second issue criterion.

The method comprises identifying, based on the determined issue, a set of candidate actions to the issue from a plurality of possible actions. The plurality of possible actions may comprise an action regarding one or more of: skin preparation, base plate and/or sensor assembly part preparation, base plate and/or sensor assembly part placement, base plate and/or sensor assembly part application, ostomy appliance type, base plate and/or sensor assembly part type, and user guidance. Identifying, based on the determined issue, a set of candidate actions to the issue from a plurality of possible actions may comprise mapping the issue to a set of candidate actions, e.g. with a look-up table in memory of the accessory device. A set of candidate actions to the issue may comprise one or more, such as a plurality of, candidate actions. Identifying, based on the determined issue, a set of candidate actions to the issue from a plurality of possible actions may comprise obtaining the set of candidate actions, e.g. from a server device. Accordingly, the method may comprise transmitting the issue to a server device and/or receiving the set of candidate actions from the server device.

A set of candidate actions to one issue, e.g. a first issue, may be different from a set of candidate actions to another issue, such as a second issue. For example, a set of candidate actions to one issue, e.g. a first issue, may have a larger number of candidate actions than a set of candidate actions to another issue, such as a second issue.

An exemplary candidate action may be a remedy. An exemplary candidate action may be change of ostomy appliance type. An exemplary candidate action may be to improve application procedure, e.g. application of optimum pressure on base plate or base plate with sensor assembly part and/or position of base plate or base plate with sensor assembly part, avoid mucus on proximal side of base plate and/or sensor assembly part, for the base plate and/or sensor assembly part. An exemplary candidate action may be to suggest use of one or more accessories, such as a sealing paste, sealing tape and/or sealing ring. An exemplary candidate action may be to improve preparation, such as cleaning and drying, of the skin surface. An exemplary candidate action may be to improve preparation, such as cutting, of the base plate and/or the sensor assembly part. The method may comprise displaying a number of candidate action user interface elements on the display, each candidate action user interface element corresponding to a candidate action of the set of candidate actions. An exemplary candidate action may be to contact nurse or professional care taker. An exemplary candidate action may be to evaluate/change intake, such as diet and/or medicine. An exemplary candidate action may be to evaluate/change physical activity, such as way of moving, movement pattern and/or physical techniques to improve wear time. An exemplary candidate action may be to evaluate/change user habits. An exemplary candidate action may be to evaluate/change clothing style, such as belt position and/or low waist/high waist clothing.

In one or more exemplary methods, identifying the set of candidate actions from a plurality of possible actions based on the determined issue comprises identifying the set of candidate actions from a plurality of possible actions based on the determined issue and on user data. The user data optionally comprises one or more of ostomate type, skin irregularity parameter, stoma position parameter, health data, nutritional data, medicine intake data, activity data, gender data, and age data. The skin irregularity parameter may be indicative of presence and/or position of scar. The skin irregularity parameter may be indicative of size and/or shape of scar. The stoma position parameter is indicative of the position of the stoma, e.g. above or below belly, distance to belly, and/or which side of the body (left/right).

The method comprises selecting, e.g. in response to a user selecting a corresponding candidate action user interface element corresponding to the candidate action, a set of digital content based on the set of candidate actions and/or the selected candidate action; and displaying the set of digital content on the display. Selecting a set of digital content may comprise obtaining, such as generating and/or retrieving from the memory of the accessory device, the set of digital content. Selecting a set of digital content may comprise obtaining the set of digital content from a server device.

In one or more exemplary methods, displaying the set of digital content on the display comprises displaying the set of digital content on the display in a first application, wherein the first application is an ostomy user application installed on the accessory device.

Displaying the set of digital content on the display may comprise displaying on the display, e.g. on a locked screen, a notification indicative of the set of digital content. In one or more exemplary methods, the method comprises detecting a second user input selecting the notification; and in response to detecting the second user input, opening the ostomy user application. Thereby is ensured that a user can see and react on an issue without unlocking the accessory device.

Displaying the set of digital content on the display may comprise displaying on the display one of more user interface elements representative of the digital content.

The digital content may comprise media content. The media content may comprise video, images and/or text. The media content may comprise a chatbot. The media content may comprise an animation. The media content may comprise augmented reality.

In one or more exemplary methods, the method comprises displaying, on the display, a second user interface element prompting the user to provide feedback on the displayed digital content and/or the identified issue.

The base plate and/or the sensor assembly part optionally comprises a plurality of electrodes configured to detect presence of fluid on the proximal side of the first adhesive layer, i.e. between the base plate and/or the sensor assembly part and the skin surface of the user, e.g. in a primary sensing zone and/or a secondary sensing zone. The plurality of electrodes may include a first leakage electrode, a second leakage electrode, and a third leakage electrode. Obtaining the monitor data may comprise obtaining monitor data indicative of detection of fluid on the proximal side in the primary sensing zone and/or the secondary sensing zone. The monitor data, e.g. the ostomy data and/or parameter data, may be indicative of resistance between any two of the plurality of electrodes, capacitance and/or inductance between any two of the plurality of electrodes, and/or any change thereof.

In one or more exemplary methods, determining an issue may comprise determining the issue as a first issue, if the monitor data or parameters based thereon satisfy a first issue criterion.

In one or more exemplary methods, determining an issue may comprise determining the issue as a first issue, e.g. if the monitor data are indicative of a moisture pattern type being an omnidirectional moisture pattern and a wear time less than a default or expected wear time. The set of candidate actions to the first issue may comprise a candidate action to improve preparation of the skin surface. The set of candidate actions to the first issue may comprise a candidate action to improve preparation, such as cutting, of the base plate and/or the sensor assembly part. The set of candidate actions to the first issue may comprise a candidate action to improve application procedure for the base plate or base plate with sensor assembly part.

In one or more exemplary methods, determining an issue may comprise determining the issue as a second issue, if the monitor data or parameters based thereon satisfy a second issue criterion.

In one or more exemplary methods, determining an issue may comprise determining the issue as a second issue, e.g. indicative of irregularities in the skin surface, if the monitor data are indicative of the same directional moisture pattern type for a number of, e.g. at least 2 or at least three, base plate and/or sensor assembly part wear time cycles. The set of candidate actions to the second issue may comprise a candidate action to suggest use of one or more accessories, such as sealing paste and/or sealing ring. The set of candidate actions to the second issue may comprise a candidate action to improve the application procedure. The set of candidate actions to the second issue may comprise a candidate action to evaluate/change clothing style, such as belt position and/or low waist/high waist clothing.

In one or more exemplary methods, determining an issue may comprise determining the issue as a third issue, if the monitor data or parameters based thereon satisfy a third issue criterion.

In one or more exemplary methods, determining an issue may comprise determining the issue as a third issue, e.g. indicative of change, e.g. reduction, of wear time, if the monitor data are indicative of a wear time different from a default, expected or average wear time. The set of candidate actions to the third issue may comprise a candidate action to evaluate/change intake, such as diet and/or medicine.

In one or more exemplary methods, determining an issue may comprise determining the issue as a fourth issue, if the monitor data or parameters based thereon satisfy a fourth issue criterion.

In one or more exemplary methods, determining an issue may comprise determining the issue as a fourth issue, e.g. indicative of a change of moisture pattern type, if the monitor data are indicative of a change from omni-directional moistory pattern type to directional moisture pattern type, optionally with a reduced wear time. The set of candidate actions to the fourth issue may comprise a candidate action to improve the application procedure. The set of candidate actions to the fourth issue may comprise a candidate action to contact nurse or professional care taker. The set of candidate actions to the fourth issue may comprise a candidate action to contact nurse or professional care taker. The set of candidate actions to the fourth issue may comprise a candidate action to evaluate/change physical activity, such as way of moving, movement pattern and/or physical techniques.

In one or more exemplary methods, determining an issue may comprise determining the issue as a fifth issue, if the monitor data or parameters based thereon satisfy a fifth issue criterion.

In one or more exemplary methods, determining an issue may comprise determining the issue as a fifth issue, if the monitor data are indicative of different directional moisture pattern types for a number of, e.g. at least two or at least three, base plate and/or sensor assembly part wear time cycles. The set of candidate actions to the fifth issue may comprise a candidate action to improve preparation, such as cutting, of the base plate and/or the sensor assembly part. The set of candidate actions to the fifth issue may comprise a candidate action to improve application procedure for the base plate and/or the sensor assembly part. The set of candidate actions to the fifth issue may comprise a candidate action to improve the preparation, such as cleaning and drying, of the skin surface. The set of candidate actions to the fifth issue may comprise a candidate action to evaluate/change physical activity, such as way of moving, movement pattern and/or physical techniques.

In one or more exemplary methods, determining an issue may comprise determining the issue as a sixth issue, if the monitor data or parameters based thereon satisfy a sixth issue criterion.

In one or more exemplary methods, determining an issue may comprise determining the issue as a sixth issue, if the monitor data are indicative of change from directional moisture pattern type to omni-directional moisture pattern type with a reduced wear time. The set of candidate actions to the sixth issue may comprise a candidate action to evaluate/change intake, such as diet and/or medicine. The set of candidate actions to the sixth issue may comprise a candidate action to improve the preparation, such as cleaning and drying, of the skin surface.

The base plate and/or the sensor assembly part comprises a first adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer has a stomal opening with a centre point or is at least prepared for forming a stomal opening with a centre point. A base plate and/or sensor assembly part according to the present disclosure enables detection of presence and/or angular position of fluid or output on the proximal side of the first adhesive layer (between a skin surface of the user and the proximal surface of the first adhesive layer).

The first adhesive layer may be made of a first composition. The first composition may comprise one or more polyisobutenes and/or styrene-isoprene-styrene. The first composition may comprise one or more hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids, and synthetic hydrocolloids. The first composition may comprise 20-60% hydrocolloids. A preferred hydrocolloid is carboxymethyl cellulose (CMC). The first composition may optionally contain other components, such as fillers, tackifiers, plasticizers, and other additives.

The primary sensing zone of the base plate and/or the sensor assembly part is optionally arranged in a primary angle space from the centre point of the first adhesive layer. The primary angle space may span a primary angle in the range from 45° to 315°, such as in the range from 45° to 135°. The primary angle may depend on the number of angular sensing zones on the base plate and/or the sensor assembly part. For example, the primary angle may be about 180°±15°, e.g. for a base plate and/or sensor assembly part with two or more sensing zones. The primary angle may be about 120°±15°, e.g. for a base plate and/or sensor assembly part with two, three or more sensing zones. The primary angle may be about 90°±15°, e.g. for a base plate and/or sensor assembly part with two, three, four or more sensing zones.

The secondary sensing zone is optionally arranged in a secondary angle space from the centre point of the first adhesive layer. The secondary angle space may span a secondary angle in the range from 45° to 315°, such as in the range from 45° to 135°. The secondary angle may depend on the number of angular sensing zones on the base plate and/or the sensor assembly part. For example, the secondary angle may be about 180°±15°, e.g. for a base plate and/or sensor assembly part with two or more sensing zones. The secondary angle may be about 120°±15°, e.g. for a base plate and/or sensor assembly part with two, three or more sensing zones. The secondary angle may be about 90°±15°, e.g. for a base plate and/or sensor assembly part with two, three, four or more sensing zones.

The plurality of electrodes may be configured to detect presence of fluid on the proximal side in a tertiary sensing zone, the tertiary sensing zone arranged in a tertiary angle space from the centre point of the first adhesive layer.

The tertiary angle space may span a tertiary angle in the range from 45° to 315°, such as in the range from 45° to 180°, for example in the range from 45° to 135°. The tertiary angle may depend on the number of angular sensing zones on the base plate and/or the sensor assembly part. For example, the tertiary angle may be about 180°±15°, e.g. for a base plate and/or sensor assembly part with three or more sensing zones. The tertiary angle may be about 120°±15°, e.g. for a base plate and/or sensor assembly part with three or more sensing zones. The tertiary angle may be about 90°±15°, e.g. for a base plate and/or sensor assembly part with three, four or more sensing zones.

The primary sensing zone and the secondary sensing zone may be separate sensing zones, i.e. non-overlapping. The primary sensing zone and the tertiary sensing zone may be separate sensing zones, i.e. non-overlapping. The secondary sensing zone and the tertiary sensing zone may be separate sensing zones, i.e. non-overlapping.

The primary sensing zone, the secondary sensing zone, and/or the tertiary sensing zone may cover electrodes embedded in the first adhesive layer as well as leakage electrodes being exposed to the surroundings. Thereby, the propagation or absorption of moisture in the first adhesive layer may be detected in one or more of the sensing zones, thereby providing for the determination of the direction of moisture propagation in the first adhesive layer. Likewise, output propagating between the skin of the wearer and the first adhesive layer may be determined by the exposed leakage electrodes. The leakage electrodes may be exposed by means of sensor point openings as described below.

The first leakage electrode may comprise one or more primary first sensing parts arranged in the primary sensing zone. The number of primary first sensing parts may be in the range from 3 to 10, e.g. 4, 5, 6 or 7. The number of primary first sensing parts may depend on the primary angle and/or the radial distance of primary first sensing parts from the centre point. The first leakage electrode may comprise one or more tertiary first sensing parts arranged in the tertiary sensing zone. The number of tertiary first sensing parts may be in the range from 3 to 10, e.g. 4, 5, 6 or 7. The number of tertiary first sensing parts may depend on the tertiary angle and/or the radial distance of tertiary first sensing parts from the centre point. In the present disclosure, a reference to ground electrode (or to fourth electrode part of the ground electrode) is a reference to the first leakage electrode. Thus, throughout the present disclosure the first leakage electrode is also referred to as or denoted ground electrode. In other words, the ground electrode acts as the first leakage electrode.

The second leakage electrode may comprise one or more primary second sensing parts arranged in the primary sensing zone. The number of primary second sensing parts may be in the range from 3 to 10, e.g. 4, 5, 6 or 7. The number of primary second sensing parts may depend on the primary angle and/or the radial distance of primary second sensing parts from the centre point. The second leakage electrode comprises one or more secondary second sensing parts arranged in the secondary sensing zone. The number of secondary second sensing parts may be in the range from 3 to 10, e.g. 4, 5, 6 or 7. The number of secondary second sensing parts may depend on the secondary angle and/or the radial distance of secondary second sensing parts from the centre point. In the present disclosure, a reference to fourth electrode is a reference to the second leakage electrode. Thus, throughout the present disclosure the second leakage electrode is also referred to as or denoted fourth electrode. In other words, the fourth electrode acts as the second leakage electrode.

The third leakage electrode may comprise one or more secondary third sensing parts arranged in the secondary sensing zone. The number of secondary third sensing parts may be in the range from 3 to 10, e.g. 4, 5, 6 or 7. The number of secondary third sensing parts may depend on the secondary angle and/or the radial distance of secondary third sensing parts from the centre point. The third leakage electrode may comprise one or more tertiary third sensing parts arranged in the tertiary sensing zone. The number of tertiary third sensing parts may be in the range from 3 to 10, e.g. 4, 5, 6 or 7. The number of tertiary third sensing parts may depend on the tertiary angle and/or the radial distance of tertiary third sensing parts from the centre point. In the present disclosure, a reference to fifth electrode is a reference to the third leakage electrode. Thus, throughout the present disclosure the third leakage electrode is also referred to as or denoted fifth electrode. In other words, the fifth electrode acts as the third leakage electrode.

Obtaining monitor data may comprise obtaining data representative of detection of fluid on the proximal side (or proximal surface) in the primary sensing zone and/or in the secondary sensing zone. The first adhesive layer may have a stomal opening with a centre point. The primary sensing zone may be arranged in a primary angle space from the centre point of the first adhesive layer and the secondary sensing zone may be arranged in a secondary angle space from the centre point of the first adhesive layer. The primary angle space may span a primary angle in the range from 45° to 315°. The secondary angle space may span a secondary angle in the range from 45° to 315°. The primary sensing zone and the secondary sensing zone may be separate sensing zones, such as non-overlapping sensing zones. The first leakage electrode may comprise one or more primary first sensing parts arranged in the primary sensing zone. The second leakage electrode may comprise one or more primary second sensing parts arranged in the primary sensing zone. The second leakage electrode may comprise one or more secondary second sensing parts arranged in the secondary sensing zone. The third leakage electrode may comprise one or more secondary third sensing parts arranged in the secondary sensing zone. Thereby, the accessory device is able to detect and distinguish between a directional leakage and an omni-directional leakage of fluid on the proximal side of the base plate and/or the sensor assembly part, which may result from different issues.

The first adhesive layer may have a plurality of sensor point openings. A sensor point opening of the first adhesive layer is configured to overlap a (sensing) part of a leakage electrode, e.g. to form a sensor point. Sensing parts of the first leakage electrode may be exposed to the proximal side of the first adhesive layer via sensor point openings in the first adhesive layer and/or masking element. Sensing parts of the second leakage electrode may be exposed to the proximal side of the first adhesive layer via sensor point openings in the first adhesive layer and/or masking element. Sensing parts of the third leakage electrode may be exposed to the proximal side of the first adhesive layer via sensor point openings in the first adhesive layer and/or masking element.

A distance between two neighbouring sensor point openings may be in the range from 1 mm to 20 mm.

A sensor point opening of the first adhesive layer may have a suitable shape and size facilitating access to a leakage electrode from the proximal side of the first adhesive layer.

A sensor point opening the first adhesive layer may have a circular or oval shape. A sensor point opening the first adhesive layer may have a shape of a rectangle or square optionally with rounded corners.

A minimum extension of a sensor point opening of the first adhesive layer may be at least 0.5 mm, such as at least 1 mm. A sufficiently large minimum extension reduces the risk of the first adhesive layer, due to the materials flow capabilities, closing the sensor point opening or at least partly or fully covering the sensing part of the corresponding leakage electrode.

A maximum extension of a sensor point opening of the first adhesive layer may be less than 20 mm.

An exemplary sensor point opening of the first adhesive layer may have a minimum extension, e.g. measured radially from the centre point, in the range from 1 mm to 4 mm and/or a maximum extension, e.g. measured circumferentially around the centre point, in the range from 2 mm to 6 mm.

The sensor point openings of the first adhesive layer may comprise primary sensor point openings. The number of primary sensor point openings may depend on the primary angle and/or the radial distance of primary sensor point openings from the centre point. In one or more exemplary base plates and/or sensor assembly parts, the number of primary sensor point openings is in the range from 5 to 20, such as in the range from 7 to 15. The primary sensor point openings may comprise one or more primary first sensor point openings and one or more primary second sensor point openings, the primary first sensor point openings configured to overlap (sensing) parts of a leakage electrode and the primary second sensor point openings configured to overlap (sensing) parts of another leakage electrode different from the leakage electrode at least partly overlapped by the primary first sensor point openings.

The sensor point openings of the first adhesive layer may comprise secondary sensor point openings. The number of secondary sensor point openings may depend on the secondary angle and/or the radial distance of secondary sensor point openings from the centre point. In one or more exemplary base plates and/or sensor assembly parts, the number of secondary sensor point openings is in the range from 5 to 20, such as in the range from 7 to 15. The secondary sensor point openings may comprise one or more secondary first sensor point openings and one or more secondary second sensor point openings, the secondary first sensor point openings configured to overlap (sensing) parts of an electrode and the secondary second sensor point openings configured to overlap (sensing) parts of another electrode different from the electrode at least partly overlapped by the secondary first sensor point openings.

The sensor point openings of the first adhesive layer may comprise tertiary sensor point openings. The number of tertiary sensor point openings may depend on the tertiary angle and/or the radial distance of tertiary sensor point openings from the centre point. In one or more exemplary base plates and/or sensor assembly parts, the number of tertiary sensor point openings is in the range from 5 to 20, such as in the range from 7 to 15. The tertiary sensor point openings may comprise one or more tertiary first sensor point openings and one or more tertiary third sensor point openings, the tertiary first sensor point openings configured to overlap (sensing) parts of a (first) leakage electrode and the tertiary third sensor point openings configured to overlap (sensing) parts of another (third) leakage electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm, such as 0.8 mm or 1.0 mm.

The first adhesive layer may have a primary thickness in a primary part of the first adhesive layer, e.g. in a primary region within a primary radial distance or in a primary radial distance range from the centre point of the stomal opening. The primary thickness may be in the range from 0.2 mm to 1.5 mm, such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the centre point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be an adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a centre point.

The second adhesive layer may be made of a second composition. The second composition may comprise one or more polyisobutenes and/or styrene-isoprene-styrene. The second composition may comprise one or more hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition may comprise 20-60% hydrocolloids. A preferred hydrocolloid is carboxymethyl cellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively, or additionally, the second adhesive layer may be thinner than the first adhesive layer. Alternatively, or additionally, the second adhesive layer may be less water and/or sweat absorbing than the first adhesive layer. Alternatively, or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data. Based on the processed ostomy data, the monitor device 6 may determine what monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine monitor data and transmit the monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a centre point 19. The size and/or shape of the stomal opening 18 is typically adjusted by the user or nurse before application of the ostomy appliance to accommodate the user's stoma.

The ostomy system 1 optionally comprises a docking station 20 forming an alternative/additional accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
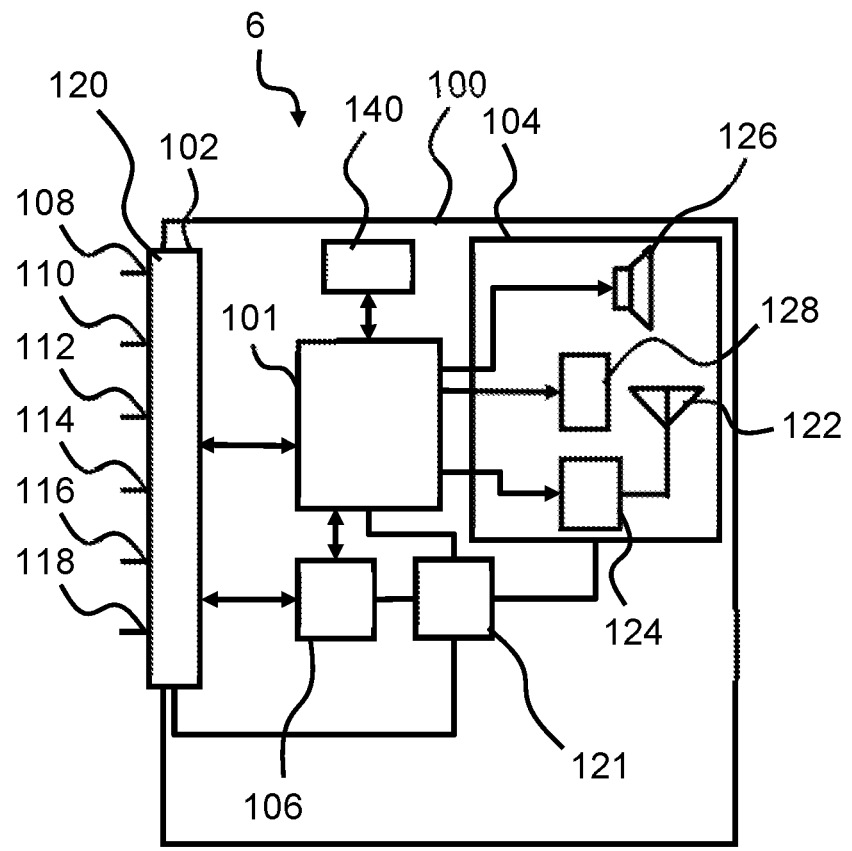
FIG. 2 illustrates an exemplary monitor device of the ostomy system.

FIG. 2 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114.

The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101. For example, the sensor unit 140 may comprise a temperature sensor for feeding temperature data to the processor and/or a G-sensor or accelerometer for feeding acceleration data to the processor 101. Additionally or alternatively, the sensor unit 140 comprises a humidity sensor and/or an acoustic sensor. The sensor unit 140 may comprise alternative and/or additional sensors suitable and/or relevant to an ostomy system as described.

The processor 101 is configured to obtain primary leakage parameter data based on the primary leakage ostomy data and obtain secondary leakage parameter data based on the secondary leakage ostomy data, wherein the primary leakage parameter data and the secondary leakage parameter data are indicative of a resistance between electrodes of the primary electrode set and the secondary electrode set, respectively. Further, the processor 101 is configured to detect presence of fluid on the proximal side of the first adhesive layer in a primary sensing zone of the base plate and/or the sensor assembly part based on the primary leakage parameter data, the primary sensing zone arranged in a primary angle space from the centre point of the first adhesive layer and to detect presence of fluid on the proximal side of the first adhesive layer in a secondary sensing zone of the base plate and/or the sensor assembly part based on the secondary leakage parameter data, the secondary sensing zone arranged in a secondary angle space from the centre point of the first adhesive layer. The processor 101 is configured to in accordance with a detection of presence of fluid in the primary sensing zone, transmit a primary leakage monitor signal comprising monitor data indicative of presence of fluid in the primary sensing zone via the second interface; and in accordance with a detection of presence of fluid in the secondary sensing zone, transmit a secondary leakage monitor signal comprising monitor data indicative of presence of fluid in the secondary sensing zone via the second interface.

For monitor device 6, the ostomy data obtained from base plate and/or sensor assembly part may comprise tertiary leakage ostomy data from a tertiary electrode set of the base plate and/or the sensor assembly part, wherein the processor 101 is optionally configured to: obtain tertiary leakage parameter data based on the primary leakage ostomy data; detect presence of fluid on the proximal side of the first adhesive layer in a tertiary sensing zone of the base plate and/or the sensor assembly part based on the tertiary leakage parameter data, the tertiary sensing zone arranged in a tertiary angle space from the centre point of the first adhesive layer; and in accordance with a detection of presence of fluid in the tertiary sensing zone, transmit a tertiary leakage monitor signal comprising monitor data indicative of presence of fluid in the tertiary sensing zone via the second interface.

In monitor device 6, to detect presence of fluid on the proximal side of the first adhesive layer in a primary sensing zone is based on a primary leakage criterion set based on the primary leakage parameter data, wherein fluid is present in the primary sensing zone if the primary leakage criteria set is satisfied, and wherein the primary leakage criteria set is based on a primary leakage threshold value stored in the memory. Further, to detect presence of fluid on the proximal side of the first adhesive layer in a secondary sensing zone is based on a secondary leakage criterion set based on the secondary leakage parameter data, wherein fluid is present in the secondary sensing zone if the secondary leakage criteria set is satisfied, and wherein the secondary leakage criteria set is based on a secondary leakage threshold value stored in the memory. Optionally and if a tertiary sensing zone is implemented, to detect presence of fluid on the proximal side of the first adhesive layer in a tertiary sensing zone is based on a tertiary leakage criteria set based on the tertiary leakage parameter data, wherein fluid is present in the tertiary sensing zone if the tertiary leakage criteria set is satisfied, and wherein the tertiary leakage criteria set is based on a tertiary leakage threshold value stored in the memory.

Figure 3:
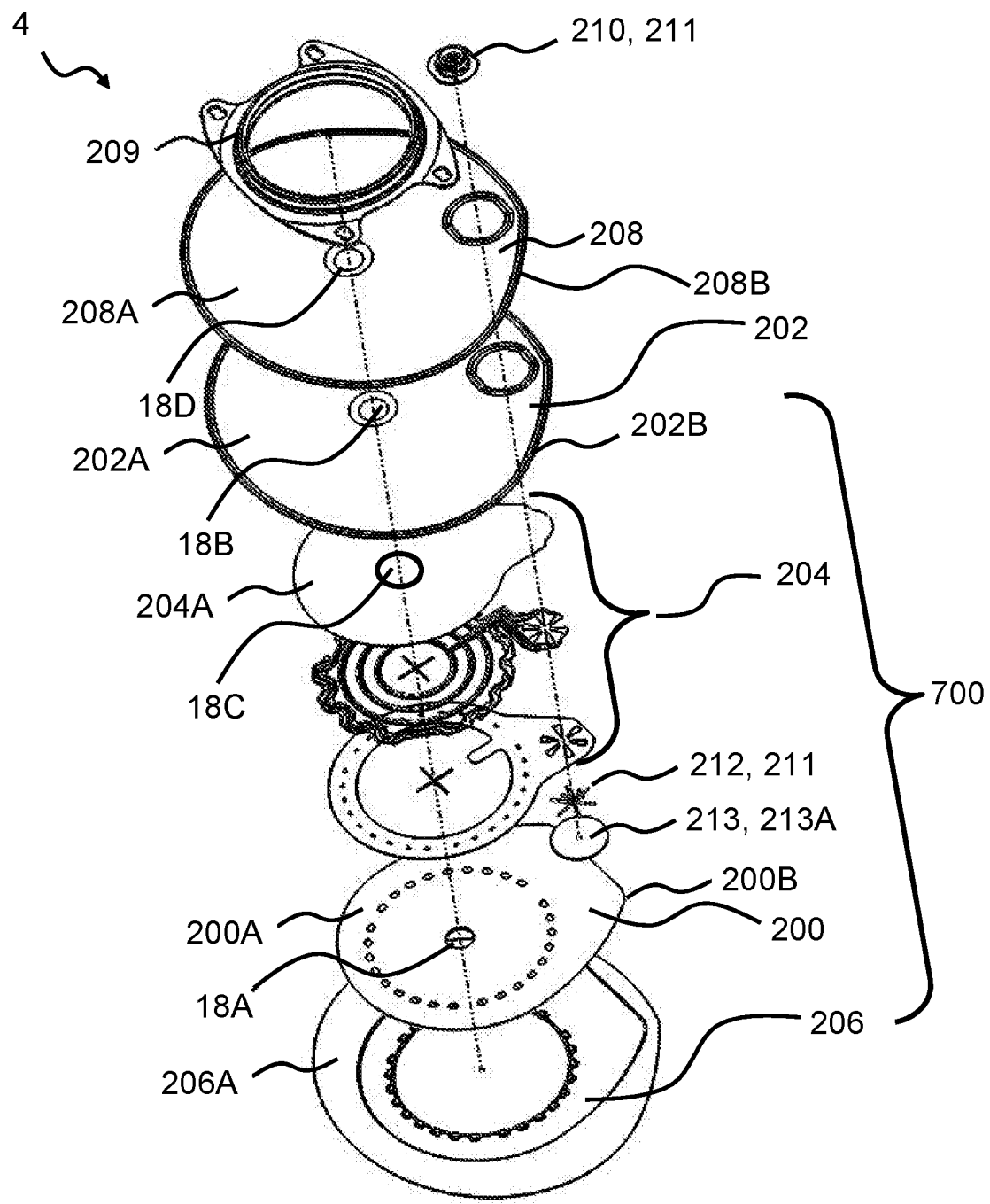
FIG. 3 is an exploded view of a base plate of an ostomy appliance.

FIG. 3 illustrates an exploded view of an exemplary base plate of an ostomy appliance. The base plate 4 comprises a first adhesive layer 200 with a stomal opening 18A. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer, with a stomal opening 18B. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with stomal opening 18C and electrodes formed on a proximal surface of the support layer. The base plate 4 comprises a release liner 206 that is peeled off by the user prior to applying the base plate 4 on the skin. The base plate 4 comprises a top layer 208 with a stomal opening 18D and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
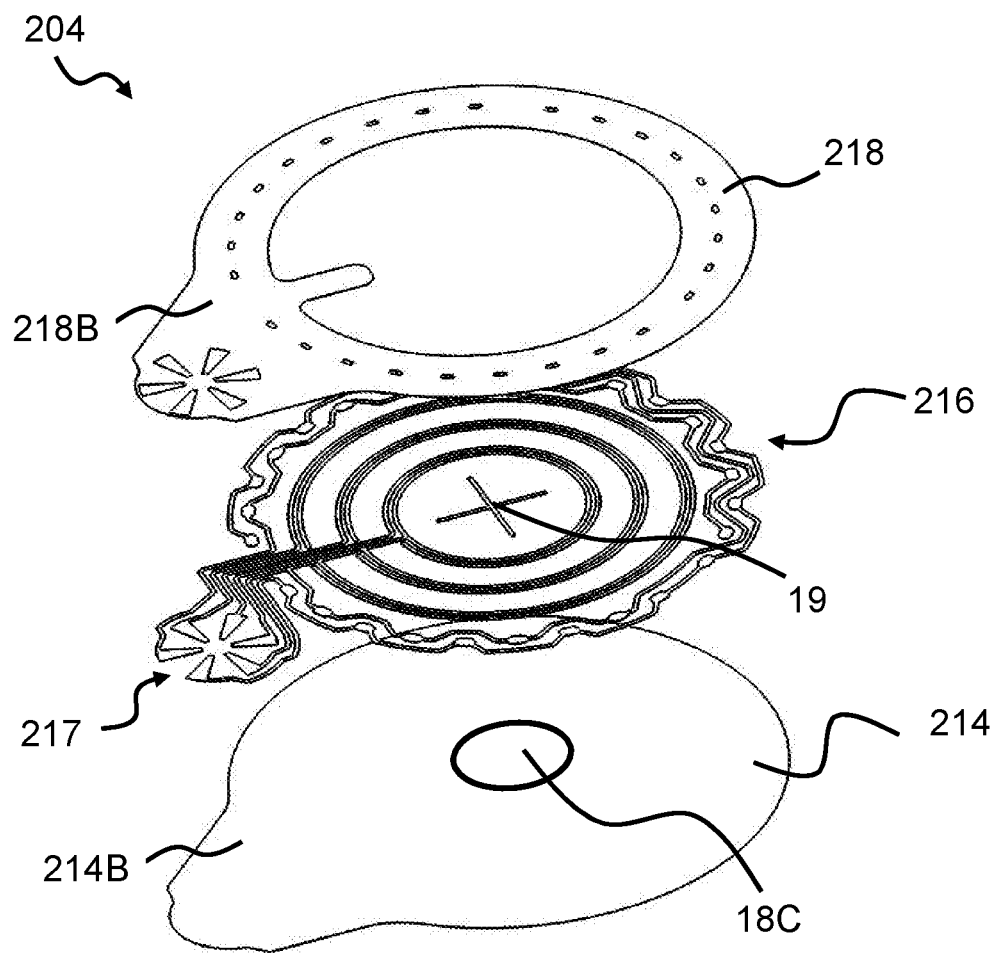
FIG. 4 is an exploded view of an exemplary electrode assembly.

FIG. 4 illustrates an exploded view of an exemplary electrode assembly 204 of a base plate and/or a sensor assembly part. The electrode assembly 204 has a distal side 204A and a proximal side 204B. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are positioned and/or formed on a proximal side 214B of the support layer 214. Further, electrode assembly 204 comprises a masking element 218 with proximal surface 218B and configured to insulate electrode parts of electrodes 216 from the first adhesive layer of the base plate and/or the sensor assembly part. The masking element 218 covers or overlap with parts of the electrodes 216 when seen in the axial direction.

Figure 5:
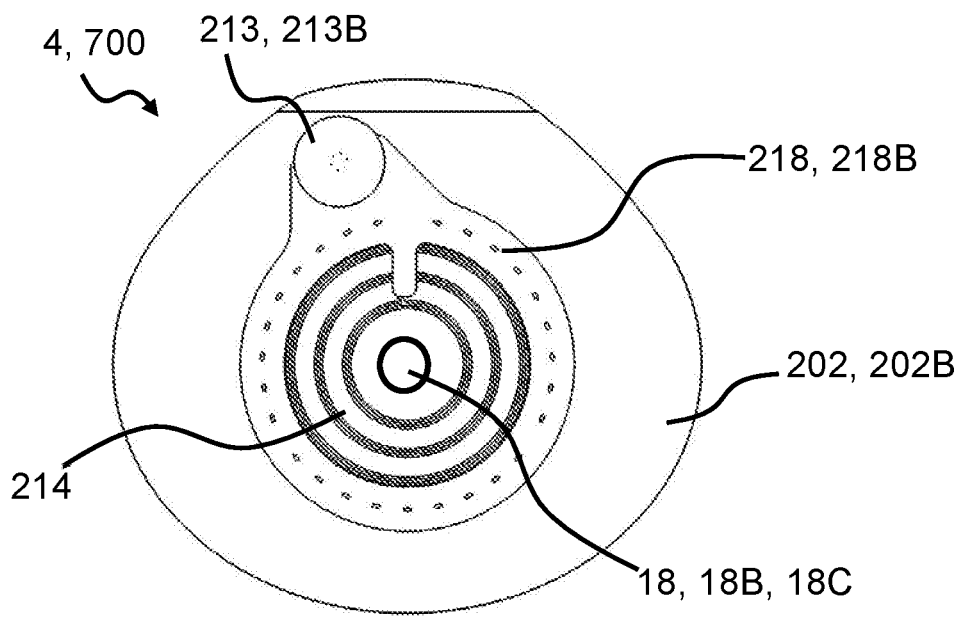
FIG. 5 is a proximal view of parts of a base plate.

FIG. 5 is a proximal view of proximal surfaces of base plate parts of the base plate and/or the sensor assembly part without the first adhesive layer and the release liner. The base plate 4 and/or the sensor assembly part 700 comprises a first intermediate element 213 on the proximal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate and/or the sensor assembly part.

Figure 6:
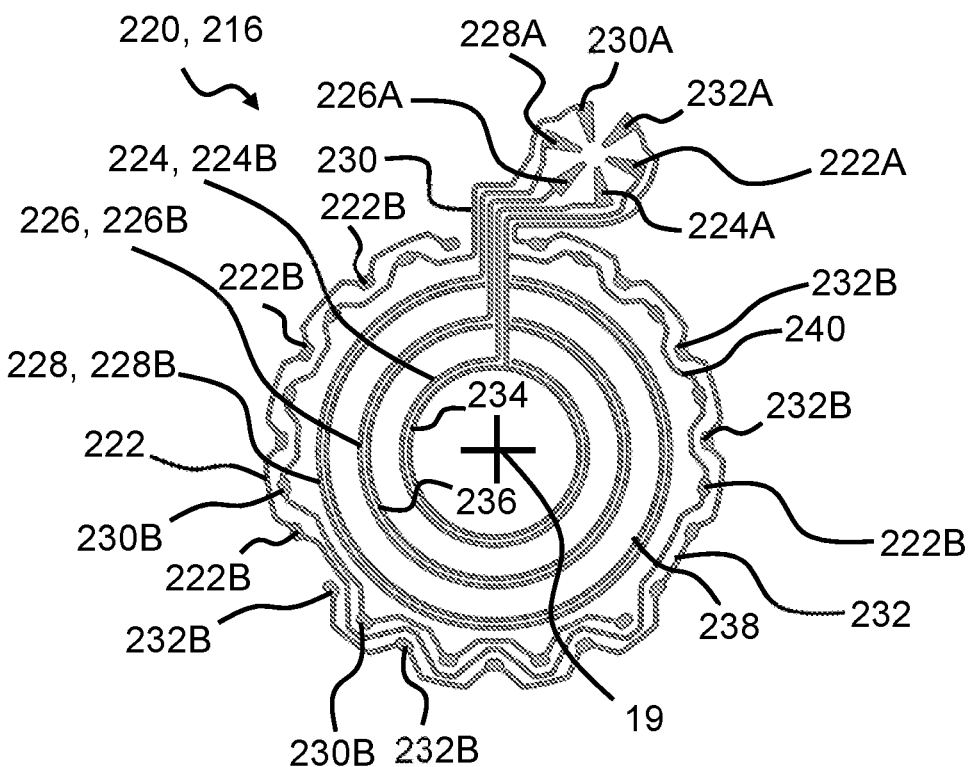
FIG. 6 is a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode (second leakage electrode) 230 comprises fourth sensing parts 230B. The fifth electrode (third leakage electrode) 232 comprises fifth sensing parts 232B.

The ground electrode 222 comprises a first electrode part 234 for forming a ground or reference for the first electrode 224. The ground electrode 222 comprises a second electrode part 236 for forming a ground or reference for the second electrode 226. The ground electrode 222 comprises a third electrode part 238 for forming a ground or reference for the third electrode 228. The masking element 218 is arranged proximal to the electrodes 222, 224, 226, 228 covering and insulating parts of the electrodes from the first adhesive and forming respective conductor parts of the electrodes 222, 224, 226, 228. The parts of the electrodes 222, 224, 226, 228 not covered by the masking element 219 contacts the first adhesive layer and form sensing parts 224B, 226B, 228B of electrodes 224, 226, 228, respectively. Further, the electrode parts 234, 236, 238 form sensing parts of the ground electrode 222.

Figure 11:
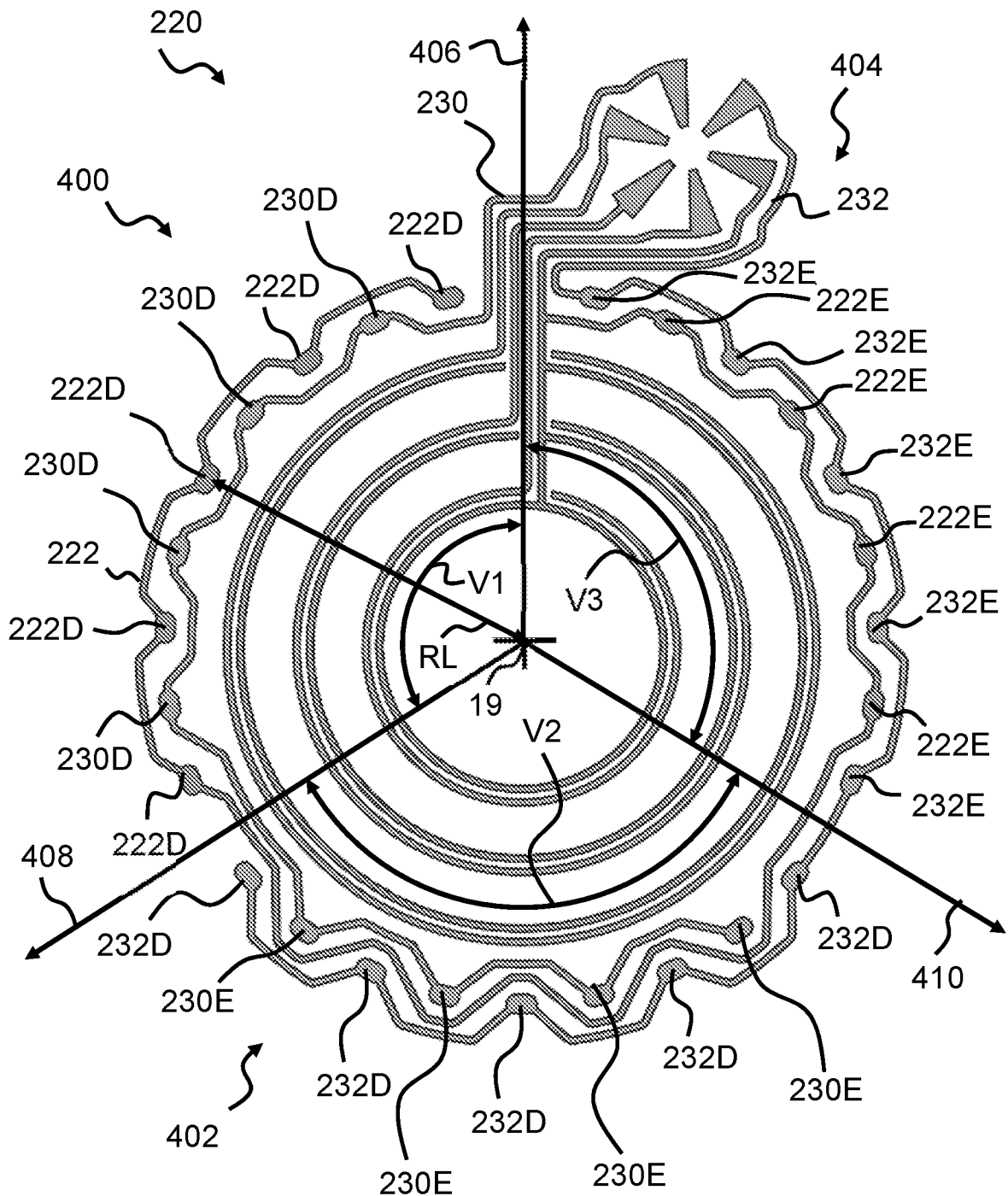
FIG. 11 is a distal view of the electrode configuration of FIG. 6.

The first sensing part 224B extends circularly at least 330 degrees around the stomal opening at a first radial distance R1 from the centre point 19, see also FIG. 11. The first radial distance R1 is 14 mm. The first electrode part 234 is arranged on the inside of the first sensing part (i.e. closer to the centre point) and extends circularly at least 330 degrees around the stomal opening at a first ground distance RG1 from the first sensing part (radially from the centre point). The first ground distance RG1 is about 1 mm.

The second sensing part 226B extends circularly at least 330 degrees around the stomal opening at a second radial distance R2 from the centre point 19, see also FIG. 11. The second radial distance R2 is 18 mm. The second electrode part 236 is arranged on the inside of the second sensing part 226B (i.e. closer to the centre point) and extends circularly at least 330 degrees around the stomal opening at a second ground distance RG2 from the second sensing part 226B (radially from the centre point). The second ground distance RG2 is about 1 mm.

The third sensing part 228B extends circularly at least 330 degrees around the stomal opening at a third radial distance R3 from the centre point 19, see also FIG. 11. The third radial distance R3 is about 26 mm. The third electrode part 238 is arranged on the inside of the third sensing part 228B (i.e. closer to the centre point) and extends circularly at least 330 degrees around the stomal opening at a third ground distance RG3 from the third sensing part 228B (radially from the centre point). The third ground distance RG3 is about 1 mm.

The ground electrode 222 comprises a fourth electrode part 240 for forming a ground or reference for the fourth electrode 230 and the fifth electrode 232. The fourth electrode part 240 of the ground electrode forms the first leakage electrode. The fourth electrode part 240 of the ground electrode 222 extends at least 300 degrees around the stomal opening and comprises ground sensing parts 222B. The fourth sensing parts 230B, fifth sensing parts 232B, and ground sensing parts of the fourth electrode part 240 are circularly distributed around the centre point 19 at a leakage radius from the centre point. The fourth sensing parts 230B, fifth sensing parts 232B, and ground sensing parts of the fourth electrode part may have a radial extension larger than 1.0 mm, such as in the range from 1.5 mm to 3.0 mm, e.g. about 2.0 mm. The fourth sensing parts 230B, fifth sensing parts 232B, and ground sensing parts of the fourth electrode part 240 may have a circumferential extension (perpendicular to the radial extension) larger than 1.0 mm, such as in the range from 2.5 mm to 5.0 mm, e.g. about 3.5 mm. In one or more exemplary base plates and/or sensor assembly parts, the electrodes 224, 226, 228 and electrode parts 234, 236, 238 may be omitted from the electrode configuration/electrode assembly.

Figure 7:
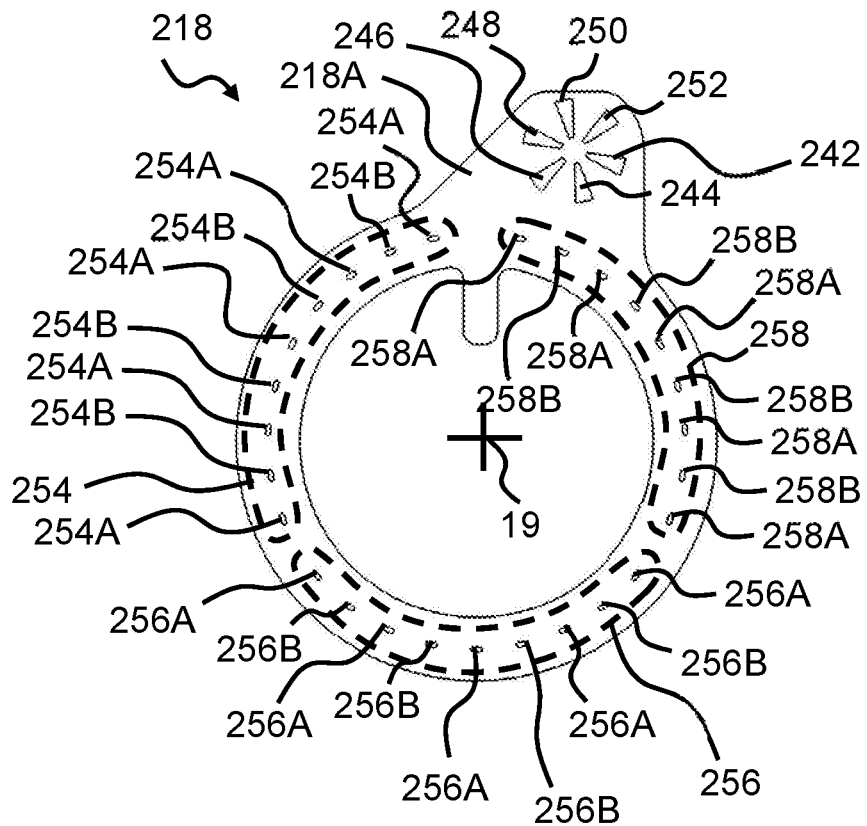
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode (first leakage electrode) 222 and/or a part of the fourth electrode (second leakage electrode) 230. The primary sensor point openings 254 comprise, in the illustrated exemplary masking element, five primary sensor point openings 254A each configured to overlap a respective sensing part of the ground electrode (first leakage electrode) 222. The primary sensor point openings 254 comprise, in the illustrated exemplary masking element, four primary sensor point openings 254B each configured to overlap a respective sensing part of the fourth electrode (second leakage electrode) 230. The sensor point openings comprise secondary sensor point openings shown within dotted line 256, each second sensor point opening configured to overlap a part of the fourth electrode (second leakage electrode) 230 and/or a part of the fifth electrode (third leakage electrode) 232. The secondary sensor point openings 256 comprise, in the illustrated exemplary masking element, five secondary sensor point openings 256A each configured to overlap a respective sensing part of the fifth electrode (third leakage electrode) 232. The secondary sensor point openings 256 comprise, in the illustrated exemplary masking element, four secondary sensor point openings 256B each configured to overlap a respective sensing part of the fourth electrode (second leakage electrode) 230. The sensor point openings comprise tertiary sensor point openings shown within dotted line 258, each tertiary sensor opening configured to overlap a part of the fifth electrode (third leakage electrode) 232 and/or a part of the ground electrode (first leakage electrode) 222. The tertiary sensor point openings 258 comprise, in the illustrated exemplary masking element, five tertiary sensor point openings 258A each configured to overlap a respective sensing part of the fifth electrode (third leakage electrode) 232. The tertiary sensor point openings 258 comprise, in the illustrated exemplary masking element, four tertiary sensor point openings 258B each configured to overlap a respective sensing part of the ground electrode (first leakage electrode) 222. The sensor point openings 254A, 254B, 256A, 256B, 258A, 258B, are circularly arranged at a leakage radius of about 30 mm from the centre point 19.

Figure 8:
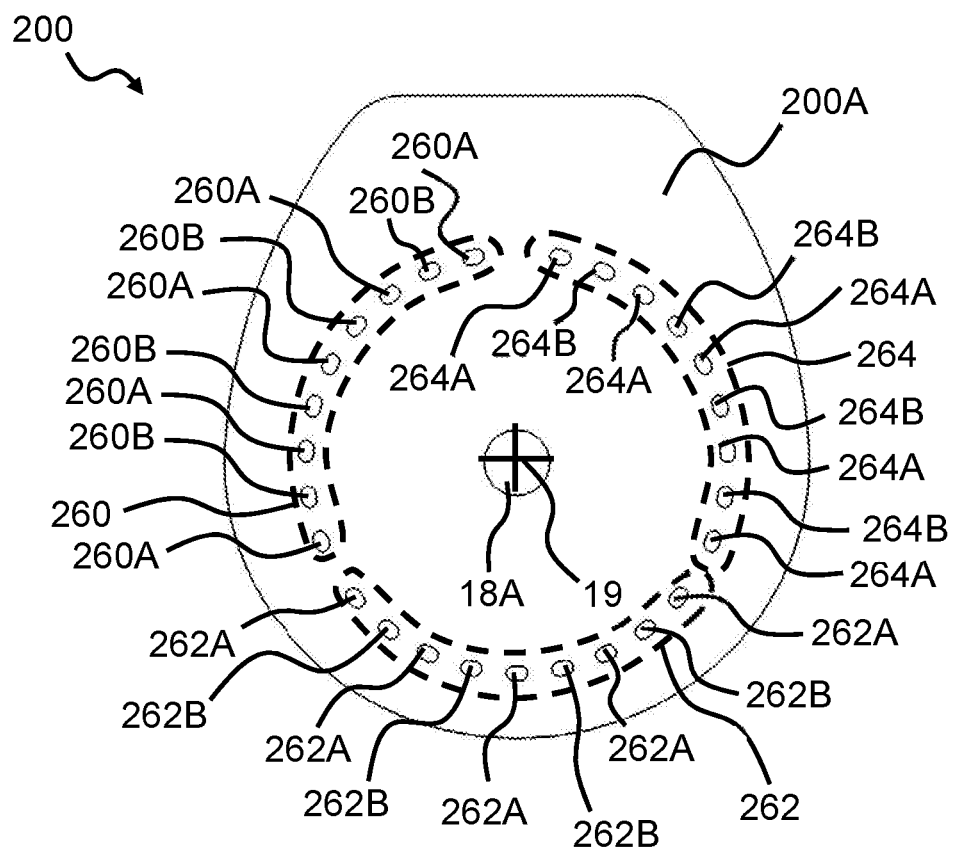
FIG. 8 is a distal view of an exemplary first adhesive layer.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings comprise, in the illustrated exemplary first adhesive layer, five primary sensor point openings 260A each configured to overlap a respective sensing part of the ground electrode 222. The primary sensor point openings comprise, in the illustrated exemplary first adhesive layer, four primary sensor point openings 260B each configured to overlap a respective sensing part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings comprise, in the illustrated exemplary first adhesive layer, five secondary sensor point openings 262A each configured to overlap a respective sensing part of the fifth electrode 232. The secondary sensor point openings comprise, in the illustrated exemplary first adhesive layer, four secondary sensor point openings 262B each configured to overlap a respective sensing part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings comprise, in the illustrated exemplary first adhesive layer, five tertiary sensor point openings 264A each configured to overlap a respective sensing part of the fifth electrode 232. The tertiary sensor point openings comprise, in the illustrated exemplary first adhesive layer, four tertiary sensor point openings 264B each configured to overlap a respective sensing part of the ground electrode 222.

Figure 9:
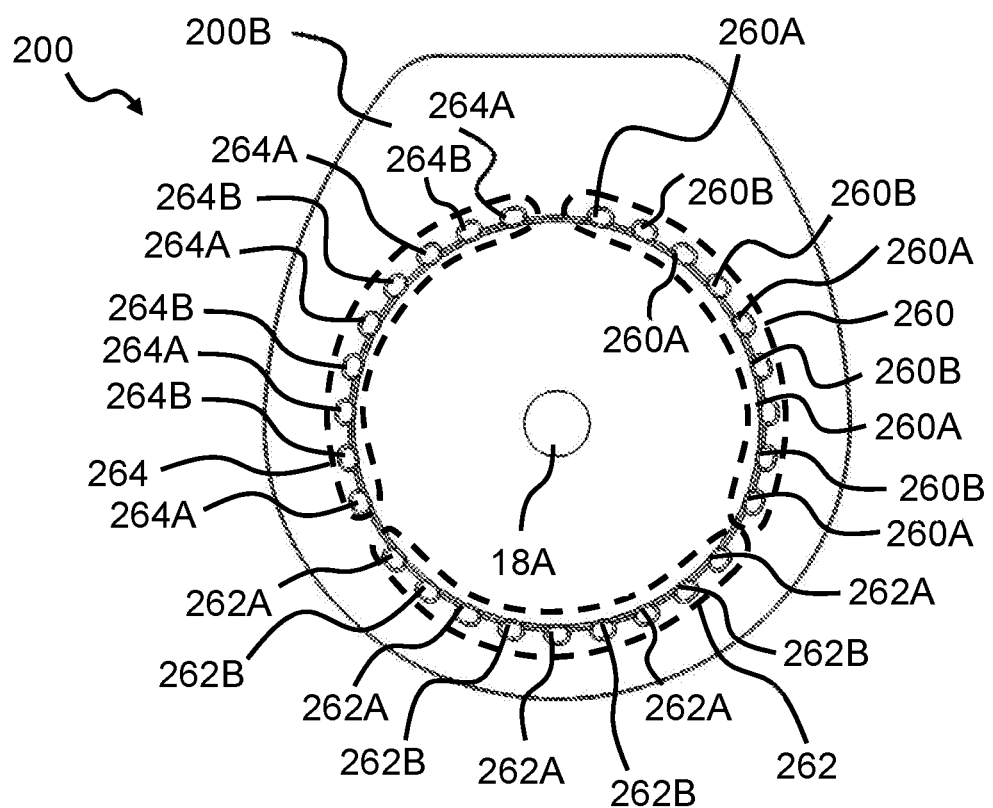
FIG. 9 is a proximal view of the first adhesive layer of FIG. 8.

FIG. 9 is a proximal view of the first adhesive layer of FIG. 8. The sensor point openings 260A, 260B, 262A, 262B, 264A, 264B, are circularly arranged at a leakage radius of about 30 mm from the centre point.

Figure 10:
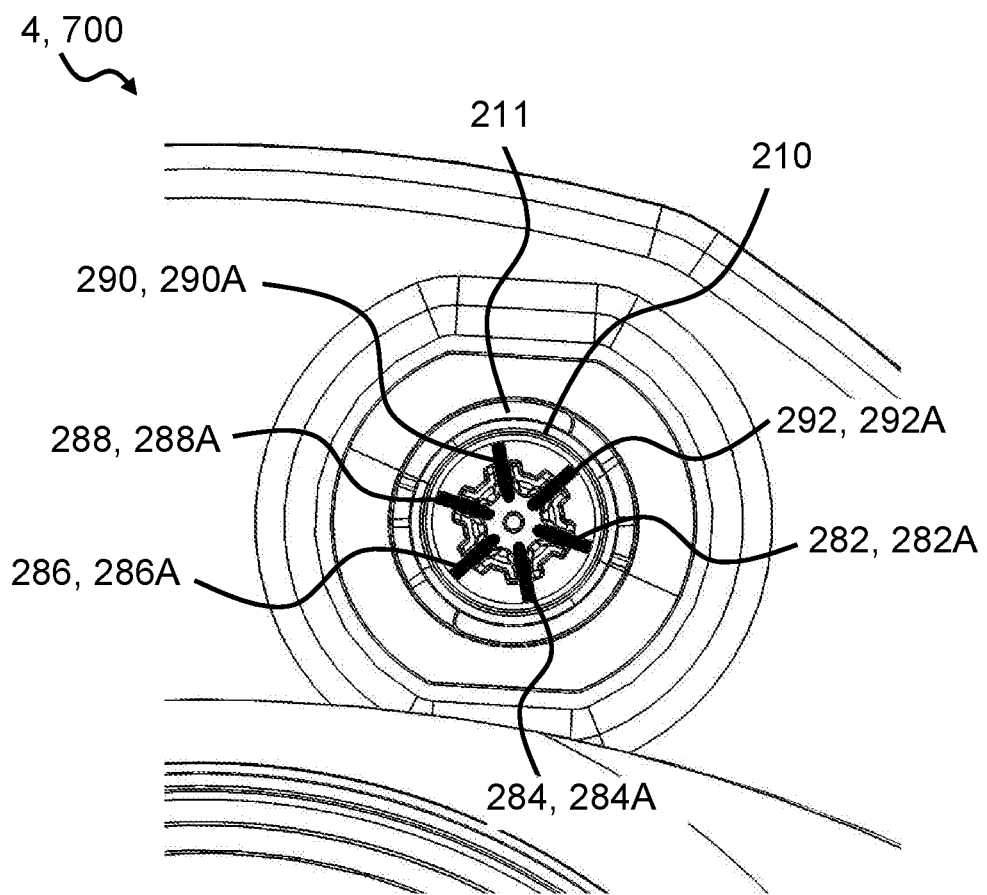
FIG. 10 is a distal view of a part of the base plate including monitor interface.

FIG. 10 is a more detailed distal view of a part of the base plate 4 and/or the sensor assembly part 700. The base plate 4 and/or the sensor assembly part 700 comprises a monitor interface. The monitor interface comprises the first connector 211. The first connector 211 comprises coupling part 210 configured to releasably couple the monitor device to the base plate and/or the sensor assembly part and thus forming a releasable coupling. The first connector 211 of the monitor interface comprises a plurality of terminals formed by respective terminal elements for forming respective electrical connections with respective terminals of the monitor device.

The plurality of terminals of the first connector 211 of the monitor interface comprises a ground terminal element 282 forming a ground terminal 282A, a first terminal element 284 forming a first terminal 284, a second terminal element 286 forming a second terminal 286A, and optionally a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate and/or the sensor assembly part, the number of terminals and the position of the terminals in the coupling part may be adapted to the electrode configuration used in the electrode assembly of the base plate and/or the sensor assembly part. For example, a first connector for a base plate and/or a sensor assembly part with the electrode configuration 220A shown in FIG. 11 comprises four terminals respectively connected to connection parts 222A, 224A, 226A, 228A of the electrodes, and a first connector for a base plate and/or a sensor assembly part with the electrode configuration 220B shown in FIG. 12 comprises three terminals respectively connected to connection parts 222A, 224A, 226A of the electrodes.

FIG. 11 is a distal view of the exemplary electrode configuration 220 of FIG. 6 for a base plate and/or a sensor assembly part. The electrode configuration 220 comprises a first leakage electrode 222, second leakage electrode 230, and third leakage electrode 232. The leakage electrodes 222, 230, 232 are configured to detect presence of fluid on the proximal side of the first adhesive layer in three angular sensing zones, primary sensing zone 400, secondary sensing zone 402, and tertiary sensing zone 404. The primary sensing zone 400 is arranged in a primary angle space between a first direction 406 and a second direction 408 from the centre point 19, wherein the primary angle space spans a primary angle V1 of 120°. The secondary sensing zone 402 is arranged in a secondary angle space between the second direction 408 and a third direction 410 from the centre point 19, wherein the secondary angle space spans a secondary angle V2 of 120°. The tertiary sensing zone 404 is arranged in a tertiary angle space between the third direction 410 and the first direction 406 from the centre point 19, wherein the tertiary angle space spans a tertiary angle V3 of 120°.

The first leakage electrode 222 comprises five primary sensing parts 222D arranged in the primary sensing zone 400, and four tertiary sensing parts 222E arranged in the tertiary sensing zone 404. Each primary sensing part 222D is aligned with a respective primary sensor point opening 254A of the masking element 218 (see FIG. 7). Further, each primary sensing part 222D is aligned with a respective primary sensor point opening 260A of the first adhesive layer 200 (see FIG. 8). Each tertiary sensing part 222E of the first leakage electrode 222 is aligned with a respective tertiary sensor point opening 258B of the masking element 218 (see FIG. 7). Further, each tertiary first sensing part 222E is aligned with a respective tertiary sensor point opening 264B of the first adhesive layer 200 (see FIG. 8).

The second leakage electrode 230 comprises four primary sensing parts 230D arranged in the primary sensing zone 400, and four secondary sensing parts 230E arranged in the secondary sensing zone 402. Each primary sensing part 230D is aligned with a respective primary sensor point opening 254B of the masking element 218 (see FIG. 7). Further, each primary sensing part 230D is aligned with a respective primary sensor point opening 260B of the first adhesive layer 200 (see FIG. 8). Each secondary sensing part 230E is aligned with a respective secondary sensor point opening 256B of the masking element 218 (see FIG. 7). Further, each secondary sensing part 230E is aligned with a respective secondary sensor point opening 262B of the first adhesive layer 200 (see FIG. 8).

The third leakage electrode 232 comprises five secondary sensing parts 232D arranged in the secondary sensing zone 402, and five tertiary sensing parts 232E arranged in the tertiary sensing zone 404. Each secondary sensing part 232D is aligned with a respective secondary sensor point opening 256A of the masking element 218 (see FIG. 7). Further, each secondary sensing part 232D is aligned with a respective secondary sensor point opening 262A of the first adhesive layer 200 (see FIG. 8). Each tertiary sensing part 232E is aligned with a respective tertiary sensor point opening 258A of the masking element 218 (see FIG. 7). Further, each tertiary sensing part 232E is aligned with a respective tertiary sensor point opening 264A of the first adhesive layer 200 (see FIG. 8).

The sensing parts 222D, 222E, 230D, 230E, 232D, 232E are circularly arranged at a leakage radius RL of about 30 mm from the centre point.

Figure 12:
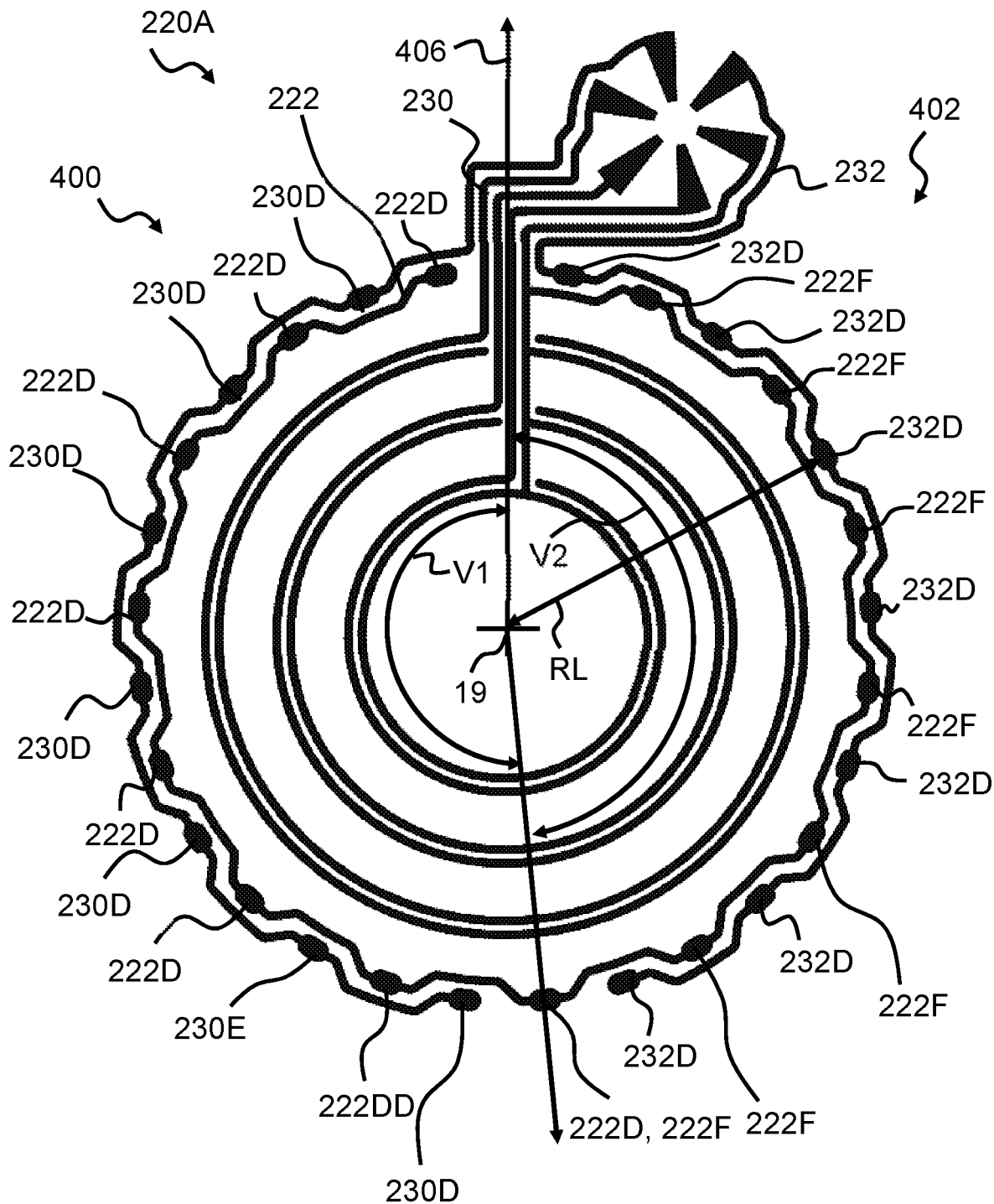
FIG. 12 is a distal view of an exemplary electrode configuration.

FIG. 12 is a distal view of an exemplary electrode configuration 220A for a base plate and/or a sensor assembly part. The electrode configuration 220 comprises a first leakage electrode 222, second leakage electrode 230, and third leakage electrode 232. The leakage electrodes 222, 230, 232 are configured to detect presence of fluid on the proximal side of the first adhesive layer in two angular sensing zones, primary sensing zone 400 and secondary sensing zone 402. The primary sensing zone 400 is arranged in a primary angle space between a first direction 406 and a second direction 408 from the centre point 19, wherein the primary angle space spans a primary angle V1 of about 185°. The secondary sensing zone 402 is arranged in a secondary angle space between the second direction 408 and the first direction 406 from the centre point 19, wherein the secondary angle space spans a secondary angle V2 of about 175°.

The first leakage electrode 222 comprises primary sensing parts 222D arranged in the primary sensing zone 400, and secondary sensing parts 222F arranged in the secondary sensing zone 402. The second leakage electrode 230 comprises primary sensing parts 230D arranged in the primary sensing zone 400. The third leakage electrode 232 comprises secondary sensing parts 232D arranged in the secondary sensing zone 402. Each primary sensing part 222D, 230D is aligned with a respective primary sensor point opening of the masking element 219 (see FIG. 13) and with a respective primary sensor point opening of the first adhesive layer 201 (see FIG. 14). The sensing parts 222D, 222F, 230D, and 232D are circularly arranged at a leakage radius RL of about 30 mm from the centre point.

Figure 13:
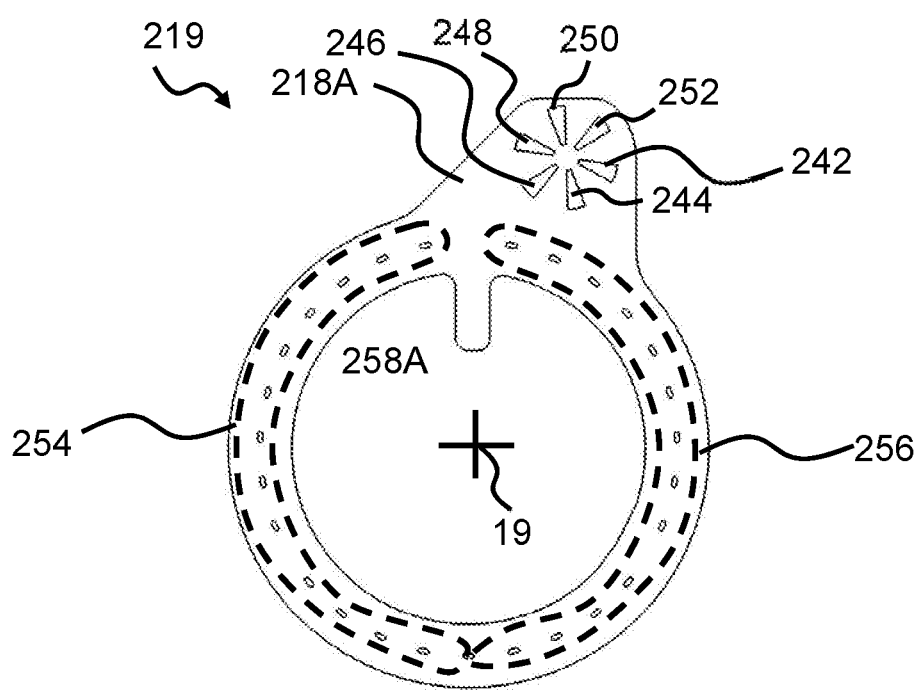
FIG. 13 is a distal view of an exemplary masking element.

FIG. 13 is a distal view of masking layer 219 for electrode configuration 220A in FIG. 12. The masking layer 219 comprises primary sensor point openings 254 in the primary angle space and secondary sensor point openings 256 in the secondary angle space.

Figure 14:
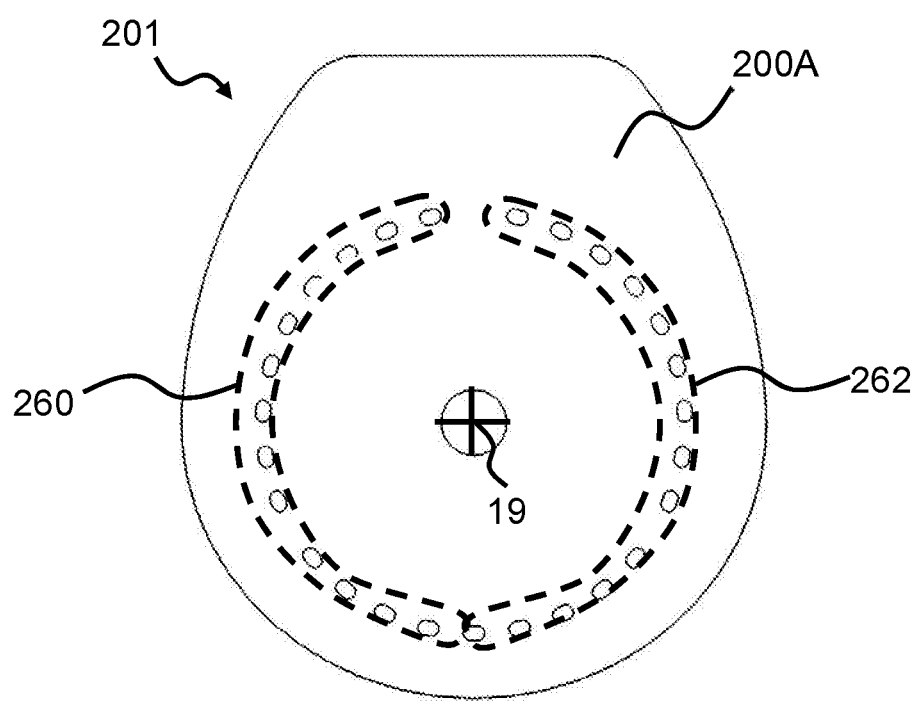
FIG. 14 is a distal view of an exemplary first adhesive layer.

FIG. 14 is a distal view of first adhesive layer 201 for electrode configuration 220A in FIG. 12 implementing a base plate and/or a sensor assembly part with two sensing zones arranged in separate angle spaces. The first adhesive layer 201 comprises primary sensor point openings 260 in the primary angle space and secondary sensor point openings 262 arranged in the secondary angle space.

Figure 15:
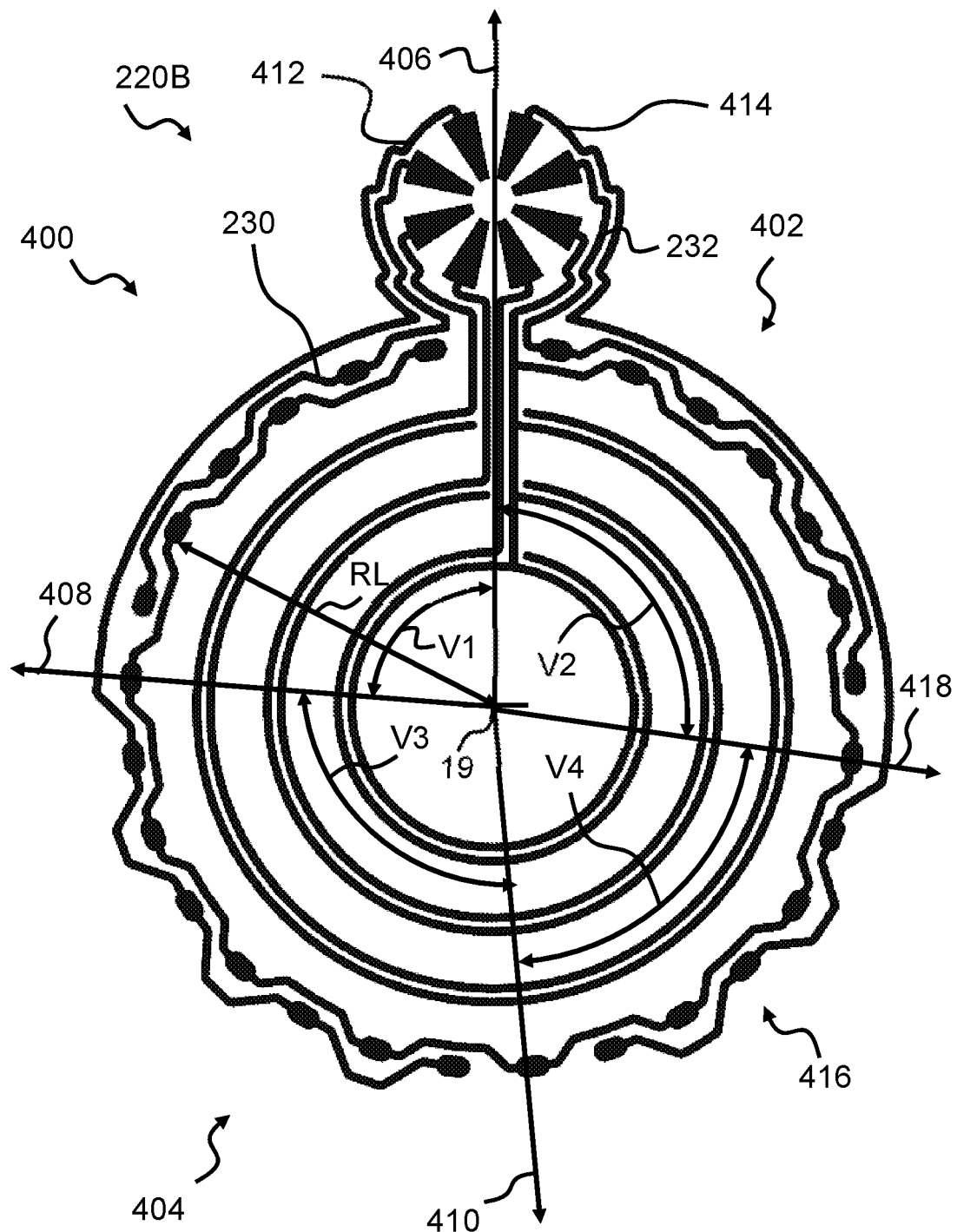
FIG. 15 is a distal view of an exemplary electrode configuration.

FIG. 15 is a distal view of an exemplary electrode configuration 220B for a base plate and/or a sensor assembly part. The electrode configuration 220B comprises first leakage electrode 222, second leakage electrode 230, third leakage electrode 232, fourth leakage electrode 412, and fifth leakage electrode 414. The leakage electrodes 222, 230, 232, 412, 414 are configured to detect presence of fluid on the proximal side of the first adhesive layer in four angular sensing zones 400, 402, 404, 416. The primary sensing zone 400 is arranged in a primary angle space spanning a primary angle V1 of about 85°. The secondary sensing zone 402 is arranged in a secondary angle space spanning a secondary angle V2 of about 95°. The tertiary sensing zone 404 is arranged in a tertiary angle space spanning a tertiary angle V3 of about 95°. The quaternary sensing zone 416 is arranged in a quaternary angle space spanning a quaternary angle V4 of about 85°.

While exemplary base plates and/or sensor assembly parts with two, three and four sensing zones have been described in more detail, the base plate and/or the sensor assembly part may comprise one or a larger number of sensing zones, such as five, six, seven, eight or more sensing zones.

Figure 16:
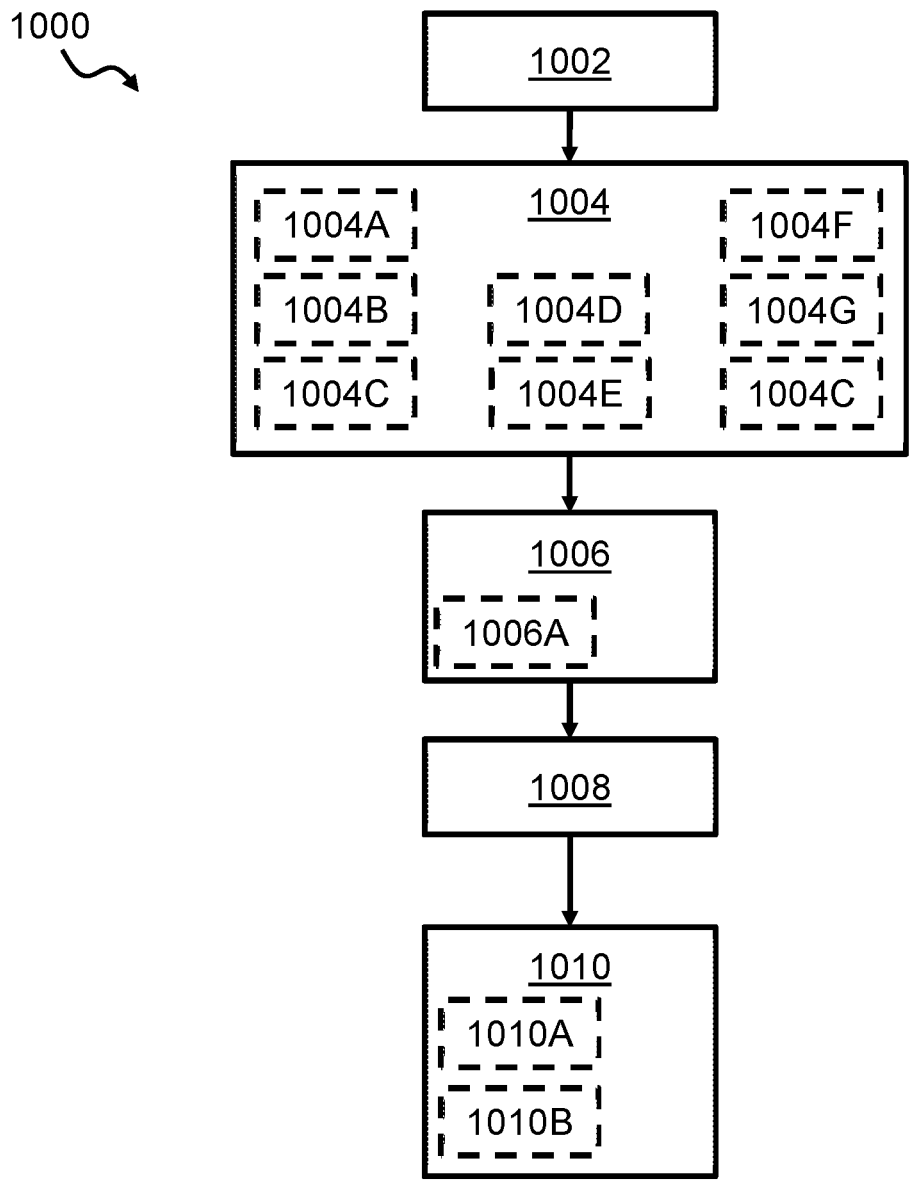
FIG. 16 is a flow diagram of an exemplary method.

FIG. 16 is a flow diagram of an exemplary method according to the present disclosure. The method 1000 is performed or at least partly performed in an accessory device, e.g. accessory device 8, wherein the accessory device comprises an interface configured to communicate with one or more devices of an ostomy system, e.g. ostomy system 1, the interface comprising a display, wherein the ostomy system comprises a monitor device, e.g. monitor device 6, and/or an ostomy appliance, e.g. ostomy appliance 2, the ostomy appliance being configured to be placed on a skin surface of a user, wherein the ostomy appliance comprises a base plate and/or a sensor assembly part, the method 1000 comprising obtaining 1002 monitor data from the monitor device, wherein the monitor data is indicative of presence of fluid at a proximal side of a first adhesive layer of the base plate and/or the sensor assembly part towards the skin surface; determining 1004 an issue based on the monitor data, wherein the issue is related to the ostomy appliance; identifying 1006, based on the determined issue, a set of candidate actions to the issue from a plurality of possible actions; selecting 1008 a set of digital content based on the set of candidate actions; and displaying 1010 the set of digital content on the display. In the method 1000, the base plate and/or the sensor assembly part optionally comprises a plurality of electrodes configured to detect presence of fluid on the proximal side in a primary sensing zone, a secondary sensing zone and optionally a tertiary sensing zone, the plurality of electrodes including a first leakage electrode, a second leakage electrode, and a third leakage electrode, and wherein obtaining the monitor data may comprise obtaining monitor data indicative of detection of fluid on the proximal side in the primary sensing zone, the secondary sensing zone and optionally the tertiary sensing zone.

The monitor data comprises ostomy data and/or parameter data based on ostomy data, wherein the ostomy data and/or parameter data is optionally indicative of resistance between any two of the plurality of electrodes, capacitance and/or inductance between any two of the plurality of electrodes, and/or any change thereof.

Determining 1004 the issue based on the monitor data may comprise determining 1004A one or more moisture pattern types based on the monitor data, wherein the issue is based on the one or more moisture pattern types. Determining 1004A one or more moisture pattern types based on the monitor data may comprise identifying a moisture pattern type based on parameter data of the monitor data. A moisture pattern type optionally comprises a moisture pattern direction.

In the method 1000, determining 1004 the issue based on the monitor data may comprise generating 1004B a set of representative features of the moisture pattern type based on previously determined moisture pattern types; determining 1004C whether one or more features of the determined moisture pattern type satisfy a first issue criterion, where in the first issue criterion is based on the set of representative features; and determining 1004D the issue as a first issue in accordance with the one or more features of the determined moisture pattern type satisfying the first issue criterion.

Determining 1004 the issue based on the monitor data optionally comprises determining 1004E a number N1 of occurrences of the determined moisture pattern type over a time period, e.g. of N base plate wear time cycles; determining 1004F whether the number of occurrences satisfies a second issue criterion; and determining 1004G the issue as a second issue in accordance with the number of occurrences satisfying the second issue criterion.

In method 1000, identifying 1006 the set of candidate actions from a plurality of possible actions based on the determined issue optionally comprises identifying 1006A the set of candidate actions from a plurality of possible actions based on the determined issue and on user data. The user data may comprise one or more of ostomate type, skin irregularity parameter, stoma position parameter, health data, nutritional data, medicine intake data, activity data, gender data, and age data.

In method 1000, displaying 1010 the set of digital content on the display optionally comprises displaying 1010A the set of digital content on the display in a first application, wherein the first application is an ostomy user application installed on the accessory device. Displaying 1010 the set of digital content on the display may comprise displaying 1010B on the display a notification indicative of the set of digital content. The set of digital content may comprise media content.

Figure 17:
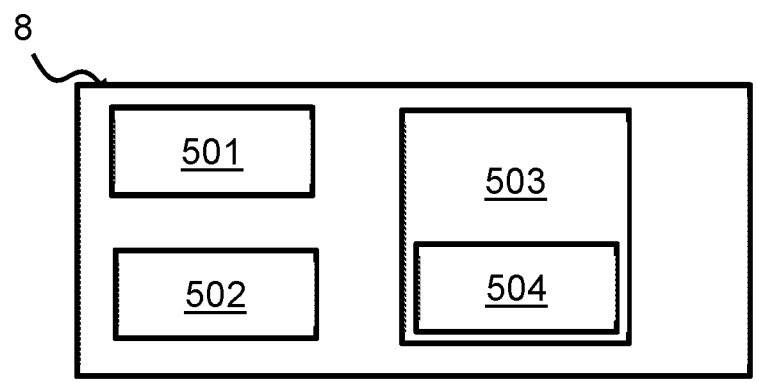
FIG. 17 illustrates an exemplary accessory device according to the present disclosure.

FIG. 17 is a block diagram illustrating an exemplary accessory device 8 according to the present disclosure. The accessory device 8 forms part of an ostomy system and is optionally configured to performing the method as disclosed herein. The accessory device 8 comprises a memory 501; a processor 502 coupled to the memory 501; and an interface 503 coupled to the processor 502. The interface 503 comprises a display 504. Peripheral devices 501, 503 can be operatively and communicably coupled to the processor 502 via a bus for communicating data. The processor 502 can be a central processing unit (CPU), but other suitable microprocessors are also contemplated.

The interface 503 is configured to communicate with one or more devices of the ostomy system. The one or more devices comprises a monitor device and/or an ostomy appliance configured to be placed on a skin surface of a user or on any additional seals. The interface 503 is configured to obtain monitor data from the one or more devices, such as to receive or retrieve the monitor data from the one or more devices. The monitor data may be indicative of a presence of fluid at a proximal side of the first adhesive layer of the ostomy appliance, such as a presence of fluid of a proximal side of the first adhesive layer of a base plate and/or a sensor assembly part of the ostomy appliance.

The processor 502 is configured to determine an issue based on the monitor data, wherein the issue is related to the ostomy appliance; identify a set of candidate actions from a plurality of possible actions based on the determined issue; select a set of digital content based on the set of candidate actions; and wherein the interface 503 is configured to display the set of digital content on the display 504.

In one or more exemplary accessory devices, to determine an issue comprises to determine a moisture pattern type and wherein the issue is based on the moisture pattern type. To determine of a moisture pattern type may comprise selecting a moisture pattern type from a set of predefined moisture pattern types. The set of predefined moisture pattern types may comprise a number K of moisture pattern types, such as at least three moisture pattern types, at least four moisture pattern types, at least five moisture pattern types. The number K of moisture pattern types may be in the range from four to twenty.

The processor 502 is optionally configured to determine one or more moisture pattern types based on the monitor data by identifying a moisture pattern type based on parameter data, such as for a corresponding sensing zone The memory 501 may be configured to store the monitor data or at least parts thereof. The processor 502 may be configured to instruct the interface 503 to display a user interface including an issue user interface element representative of the issue on the display 504. The processor 502 may be configured to instruct the interface 503 to display a user interface including a number of candidate action user interface elements on the display 504, each candidate action user interface element corresponding to a candidate action of the set of candidate actions. The processor 502 may be configured to instruct the interface 503 to display the set of digital content on the display 504, e.g. in accordance with detection of a user selection of the corresponding candidate action user interface element.

The processor 502 may be configured to determine an issue based on the monitor data obtained. The issue is indicative of the dynamic internal state of the ostomy appliance (for example early presence of fluid that is not visible to the user when the ostomy appliance is worn), related to the leakage of output (e.g. faecal material), such as severity, imminence, timing of leakage at a proximal side (or proximal surface) of the ostomy appliance. Presence of fluid on the proximal side (or proximal surface) of the first adhesive layer may affect the adhesive performance of the ostomy appliance.

Figure 18:
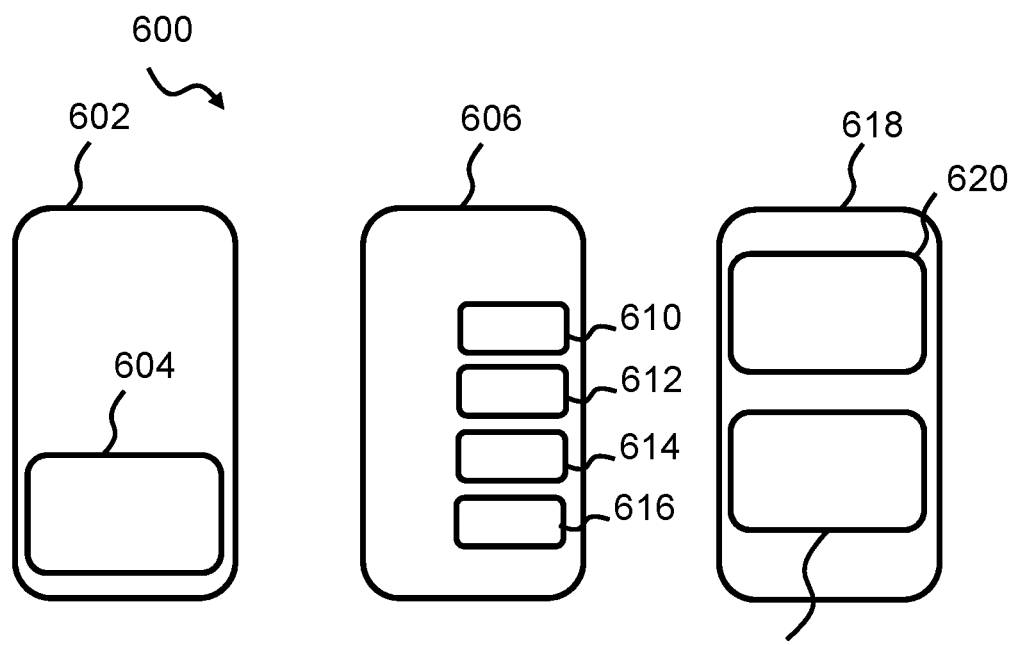
FIG. 18 illustrates an exemplary user interface of an accessory device according to the present disclosure.

FIG. 18 illustrates an exemplary user interface 600 of an accessory device according to the present disclosure. In the illustrated example, the accessory device has determined the issue as an issue of generally smaller wear time than expected for base plates and/or sensor assembly parts based on the monitor data, i.e. the monitor data are indicative of a wear time or average wear time less than an expected wear time. The user interface 600 comprises a first user interface screen 602 comprising an issue user interface element 604 in the form of a text field representative of the issue on the display 504. The accessory device/processor identifies, based on the determined issue, a set of candidate actions. The user interface 600 comprises, e.g. as part of the first user interface screen 602 or as part of a second user interface screen 606 as illustrated, a number of candidate action user interface elements 610, 612, 614, 616, each candidate action user interface element 610, 612, 614, 616 corresponding to a candidate action of the set of candidate actions. The candidate action related to first candidate action user interface element 610 is improved preparation, e.g. cutting, of the base plate and/or the sensor assembly part. The candidate action related to second candidate action user interface element 612 is improved preparation, e.g. cleaning and drying, of the skin surface. The candidate action related to third candidate action user interface element 614 is improved application, e.g. positioning, of the base plate and/or the sensor assembly part. The candidate action related to fourth candidate action user interface element 616 is change of ostomy appliance type. The accessory device/processor is configured to select a set of digital content based on the set of candidate actions and display the set of digital content on the display, e.g. as part of user interface 600 in a user interface screen upon detection of user selection of a candidate action user interface element 610, 612, 614, 616. In FIG. 18, the user interface 600 comprises a third user interface screen 618 with text 620 and a video 622 as digital content on the display 504. The third user interface screen 618 with the set of digital content 620, 622 is displayed upon detection of user selection of first candidate action user interface element 610 relating to improved cutting of the base plate and/or the sensor assembly part.

The use of the terms "first", "second", "third", "fourth", "fifth", "sixth", "primary", "secondary", "tertiary" etc. does not imply any particular order but are included to identify individual elements. Moreover, the use of the terms "first", "second", "third", "fourth", "fifth", "sixth", "primary", "secondary", "tertiary" etc. does not denote any order or importance, but rather the terms "first", "second", "third", "fourth", "fifth", "sixth", "primary", "secondary", "tertiary" etc. are used to distinguish one element from another. Note that the words "first", "second", "third", "fourth", "fifth", "sixth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

Embodiments of the present disclosure are set out in the following items:

1. A method, performed in an accessory device, wherein the accessory device comprises an interface configured to communicate with one or more devices of an ostomy system, the interface comprising a display, wherein the ostomy system comprises a monitor device and/or an ostomy appliance, the ostomy appliance being configured to be placed on a skin surface of a user, wherein the ostomy appliance comprises a sensor assembly part, the method comprising:
    obtaining monitor data from the monitor device, wherein the monitor data is indicative of presence of fluid at a proximal side of a first adhesive layer of the sensor assembly part towards the skin surface;
    determining an issue based on the monitor data, wherein the issue is related to the ostomy appliance;
    identifying, based on the determined issue, a set of candidate actions to the issue from a plurality of possible actions;
    selecting a set of digital content based on the set of candidate actions; and
    displaying the set of digital content on the display.
2. Method according to item 1, wherein the sensor assembly part comprises a plurality of electrodes configured to detect presence of fluid on the proximal side in a primary sensing zone and a secondary sensing zone, the plurality of electrodes including a first leakage electrode, a second leakage electrode, and a third leakage electrode, and wherein obtaining the monitor data comprises obtaining monitor data indicative of detection of fluid on the proximal side in the primary sensing zone and/or the secondary sensing zone.
3. Method according to any of the previous items, wherein the monitor data comprises ostomy data and/or parameter data.
4. Method according to item 3, wherein the ostomy data and/or parameter data is indicative of resistance between any two of the plurality of electrodes, capacitance and/or inductance between any two of the plurality of electrodes, and/or any change thereof.
5. Method according to any of the previous items, wherein determining the issue based on the monitor data comprises determining one or more moisture pattern types based on the monitor data.
6. Method according to item 5, wherein determining one or more moisture pattern types based on the monitor data comprises identifying a moisture pattern type based on parameter data.
7. Method according to any of items 5-6, wherein a moisture pattern type comprises a moisture pattern direction.
8. Method according to any of items 5-7, wherein determining the issue based on the monitor data comprises:
    generating a set of representative features of the moisture pattern type based on previously determined moisture pattern types;
    determining whether one or more features of the determined moisture pattern type satisfy a first issue criterion, where in the first issue criterion is based on the set of representative features; and
    determining the issue as a first issue in accordance with the one or more features of the determined moisture pattern type satisfying the first issue criterion.
9. Method according to any of items 5-8 as dependent on item 8, wherein determining the issue based on the monitor data comprises:
    determining a number of occurrences of the determined moisture pattern type over a time period;
    determining whether the number of occurrences satisfies a second issue criterion; and
    determining the issue as of a second type in accordance with the number of occurrences satisfying the second issue criterion.
10. Method according to any of the previous items, wherein identifying the set of candidate actions from a plurality of possible actions based on the determined issue comprises identifying the set of candidate actions from a plurality of possible actions based on the determined issue and on user data; wherein the user data comprises one or more of ostomate type, skin irregularity parameter, stoma position parameter, health data, nutritional data, medicine intake data, activity data, gender data, and age data.
11. Method according to any of the previous items, wherein possible actions comprise an action regarding one or more of: skin preparation, sensor assembly part preparation, sensor assembly part placement, sensor assembly part application, ostomy appliance type, sensor assembly part type, ostomy appliance type, and user guidance.
12. Method according to any of the previous items, wherein displaying the set of digital content on the display comprises displaying the set of digital content on the display in a first application, wherein the first application is an ostomy user application installed on the accessory device.
13. Method according to any of the previous items, wherein displaying the set of digital content on the display comprises displaying on the display a notification indicative of the set of digital content.
14. Method according to any of the previous items, wherein the set of digital content comprises media content.
15. An accessory device, wherein the accessory device forms part of an ostomy system, the accessory device comprising:
    a memory;
    a processor operatively connected to the memory; and an interface operatively connected to the processor and configured to communicate with one or more devices of the ostomy system, the one or more devices comprising a monitor device and/or an ostomy appliance configured to be placed on a skin surface of a user, the ostomy appliance comprising a sensor assembly part, wherein the interface is configured to obtain monitor data from the one or more devices, and
wherein the interface comprises a display,
wherein the processor is configured to
 determine an issue based on the monitor data, wherein the issue is related to the ostomy appliance;
 identify a set of candidate actions from a plurality of possible actions based on the determined issue;
 select a set of digital content based on the set of candidate actions; and
wherein the interface is configured to display the set of digital content on the display.

LIST OF REFERENCES 1 ostomy system
2 ostomy appliance
4 base plate
6 monitor device
8 accessory device
10 server device
12 network
14 coupling member
16 coupling ring
18, 18A, 18B, 18C, 18D stomal opening
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200, 201 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
217 connection parts of electrodes
218, 219 masking element
218A distal surface of masking element
218B proximal surface of masking element
220, 220A, 220B electrode configuration
222 ground electrode, first leakage electrode
222A ground connection part
222B ground sensing part, sensing part of first leakage electrode
222C ground connector part
222D primary sensing part
222E tertiary sensing part
222F secondary sensing part
224 first electrode
224A first connection part
224B first sensing part
224C first conductor part
226 second electrode
226A second connection part
226B second sensing part
226C second conductor part
228 third electrode
228A third connection part
228B third sensing part
228C third conductor part
230 fourth electrode, second leakage electrode
230A fourth connection part
230B fourth sensing part, sensing part of second leakage electrode
230D primary sensing part
230E secondary sensing part
232 fifth electrode, third leakage electrode
232A fifth connection part
232B fifth sensing part, sensing part of third leakage electrode
232D secondary sensing part
232E tertiary sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary sensor point opening for the ground electrode (first leakage electrode)
254B primary sensor point opening for the fourth electrode (second leakage electrode)
256 secondary sensor point openings of masking element
256A secondary sensor point opening for the fifth electrode (third leakage electrode)

256B secondary sensor point opening for the fourth electrode (second leakage electrode)
258 tertiary sensor point openings of masking element
258B tertiary sensor point opening for the fifth electrode (third leakage electrode)
258A tertiary sensor point opening for the ground electrode (first leakage electrode)
260 primary sensor point openings of first adhesive layer
260A primary sensor point opening for the ground electrode (first leakage electrode)
260B primary sensor point opening for the fourth electrode (second leakage electrode)
262 secondary sensor point openings of first adhesive layer
262A secondary sensor point opening for the fifth electrode (third leakage electrode)
262B secondary sensor point opening for the fourth electrode (second leakage electrode)
264 tertiary sensor point openings of first adhesive layer
264A tertiary sensor point opening for the fifth electrode (third leakage electrode)
264B tertiary sensor point opening for the ground electrode (first leakage electrode)
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
400 primary sensing zone
402 secondary sensing zone
404 tertiary sensing zone
406 first direction/zero direction
408 second direction
410 third direction
412 fourth leakage electrode
414 fifth leakage electrode
416 quaternary sensing zone
418 fourth direction
501 memory
502 processor
503 interface
504 display
600 user interface
602 first user interface screen
604 issue user interface element
606 second user interface screen
610 first candidate action user interface element
612 second candidate action user interface element
614 third candidate action user interface element
616 fourth candidate action user interface element
618 third user interface screen
620 text
622 video
700 sensor assembly part
1000 method
1002 obtaining monitor data from the monitor device
1004 determining an issue based on the monitor data
1004A determining one or more moisture pattern types based on the monitor data
1004B generating a set of representative features of the moisture pattern type based on previously determined moisture pattern types
1004C determining whether one or more features of the determined moisture pattern type satisfy a first issue criterion
1004D determining the issue as a first issue in accordance with the one or more features of the determined moisture pattern type satisfying the first issue criterion
1004E determining a number of occurrences of the determined moisture pattern type over a time period
1004F determining whether the number of occurrences satisfies a second issue criterion
1004G determining the issue as a second issue in accordance with the number of occurrences satisfying the second issue criterion
1006 identifying, based on the determined issue, a set of candidate actions to the issue from a plurality of possible actions
1006A identifying the set of candidate actions from a plurality of possible actions based on the determined issue and on user data
1008 selecting a set of digital content based on the set of candidate actions
1010 displaying the set of digital content on the display
1010A displaying the set of digital content on the display in a first application, wherein the first application is an ostomy user application installed on the accessory device
1010B displaying on the display a notification indicative of the set of digital content
R1 first radial distance
RG1 first ground distance
R2 second radial distance
RG2 second ground distance
R3 third radial distance
RG3 third ground distance
RL leakage radius
V1 primary angle
V2 secondary angle
V3 tertiary angle
V4 quaternary angle

The invention claimed is:

1. A method, performed in an accessory device, wherein the accessory device comprises an interface configured to communicate with one or more devices of an ostomy system, the interface comprising a display, wherein the ostomy system comprises a monitor device and/or an ostomy appliance, the ostomy appliance being configured to be placed on a skin surface of a user, wherein the ostomy appliance comprises a base plate, the method comprising:
obtaining monitor data from the monitor device, wherein the monitor data is indicative of presence of fluid at a proximal side of a first adhesive layer of the base plate towards the skin surface;
determining, based on the monitor data, one or more moisture pattern types and a problem related to the ostomy appliance that corresponds to the one or more moisture pattern types, wherein each moisture pattern type of the one or more moisture pattern types indicates at least one of a moisture pattern direction or a sensing zone of the base plate in which leakage is detected;
identifying, based on the determined problem, an associated candidate action from a plurality of possible actions that is a remedy to the determined problem;

selecting a set of digital content based on the identified candidate action;
displaying the set of digital content on the display.

2. The method according to claim 1, wherein the base plate comprises a plurality of electrodes configured to detect presence of fluid on the proximal side in a primary sensing zone and a secondary sensing zone, the plurality of electrodes including a first leakage electrode, a second leakage electrode, and a third leakage electrode, and wherein obtaining the monitor data comprises obtaining monitor data indicative of detection of fluid on the proximal side in the primary sensing zone and/or the secondary sensing zone.

3. The method according to claim 1, wherein the monitor data comprises ostomy data and/or parameter data.

4. The method according to claim 3, wherein the ostomy data and/or parameter data is indicative of resistance between any two of the plurality of electrodes, capacitance and/or inductance between any two of the plurality of electrodes, and/or any change thereof.

5. The method according to claim 1, wherein determining one or more moisture pattern types based on the monitor data comprises identifying at least one moisture pattern type based on parameter data.

6. The method according to claim 1, wherein at least one moisture pattern type of the one or more moisture pattern types indicates a proximity of a stoma to a sensing zone in which leakage is detected.

7. The method according to claim 1, wherein determining the problem based on the monitor data comprises:
generating a set of representative features of the moisture pattern type based on previously determined moisture pattern types;
determining whether one or more features of the determined moisture pattern type satisfy a first problem criterion, wherein the first problem criterion is based on the set of representative features; and
determining the problem as a first problem in accordance with the one or more features of the determined moisture pattern type satisfying the first problem criterion.

8. The method according to claim 7, wherein determining the problem based on the monitor data comprises:
determining a number of occurrences of the determined moisture pattern type over a time period;
determining whether the number of occurrences satisfies a second problem criterion; and
determining the problem as of a second type in accordance with the number of occurrences satisfying the second problem criterion.

9. The method according to claim 1, wherein the candidate action is identified from the plurality of possible actions based on user data, comprising one or more of ostomy appliance type, skin irregularity parameter, stoma position parameter, health data, nutritional data, medicine intake data, activity data, gender data, and age data.

10. The method according to claim 1, wherein the plurality of possible actions comprises an action regarding one or more of: skin preparation, base plate preparation, base plate placement, base plate application, ostomy appliance type, base plate type, and user guidance.

11. The method according to claim 1, wherein displaying the set of digital content on the display comprises displaying the set of digital content on the display in a first application, wherein the first application is an ostomy user application installed on the accessory device.

12. The method according to claim 1, wherein displaying the set of digital content on the display comprises displaying on the display a notification indicative of the set of digital content.

13. The method according to claim 1, wherein the set of digital content comprises media content.

14. The method according to claim 1, wherein:
determining the problem comprises comparing the determined one or more moisture pattern types with a default moisture pattern type;
the problem comprises a change in moisture pattern type between the one or more moisture pattern types and the default moisture pattern type; and
the default moisture pattern type is based on monitor data for a previous base plate wear cycle of the user.

15. An accessory device, wherein the accessory device forms part of an ostomy system, the accessory device comprising:
a memory;
a processor operatively connected to the memory; and
an interface operatively connected to the processor and configured to communicate with one or more devices of the ostomy system, the one or more devices comprising a monitor device and/or an ostomy appliance configured to be placed on a skin surface of a user, the ostomy appliance comprising a base plate, wherein the interface is configured to obtain monitor data from the one or more devices, and wherein the interface comprises a display,
wherein the processor is configured to:
determine, based on the monitor data, one or more moisture pattern types and a problem related to the ostomy appliance that corresponds to the one or more moisture pattern types, wherein each moisture pattern type of the one or more moisture pattern types indicates at least one of a moisture pattern direction or a sensing zone of the base plate in which leakage is detected;
identify a candidate action from a plurality of possible actions based on the determined problem that is a remedy to the determined problem;
select a set of digital content based on the identified candidate action; and
wherein the interface is configured to display the set of digital content on the display.

16. The accessory device according to claim 15, wherein determining one or more moisture pattern types based on the monitor data comprises identifying at least one moisture pattern type based on parameter data.

17. The accessory device according to claim 15, wherein at least one moisture pattern type of the one or more moisture pattern types indicates a proximity of a stoma to a sensing zone in which leakage is detected.

18. The accessory device of claim 15, wherein determining the problem based on the monitor data comprises:
generating a set of representative features of the moisture pattern type based on previously determined moisture pattern types;
determining whether one or more features of the determined moisture pattern type satisfy a first problem criterion, wherein the first problem criterion is based on the set of representative features; and
determining the problem as a first problem in accordance with the one or more features of the determined moisture pattern type satisfying the first problem criterion.

19. The accessory device of claim 15, wherein the candidate action is identified from the plurality of possible actions based on user data, comprising one or more of ostomy appliance type, skin irregularity parameter, stoma position parameter, health data, nutritional data, medicine intake data, activity data, gender data, and age data.

20. The accessory device of claim 15, wherein the plurality of possible actions comprises an action regarding one or more of: skin preparation, base plate preparation, base plate placement, base plate application, ostomy appliance type, base plate type, and user guidance.

\* \* \* \* \*